US012186451B2

(12) United States Patent
Niklason et al.

(10) Patent No.: US 12,186,451 B2
(45) Date of Patent: Jan. 7, 2025

(54) BIOARTIFICIAL VASCULAR PANCREAS

(71) Applicant: YALE UNIVERSITY, New Haven, CT (US)

(72) Inventors: Laura Niklason, Greenwich, CT (US); Edward Han, Montville, NJ (US)

(73) Assignee: Yale University, New Haven, CT (US)

( * ) Notice: Subject to any disclaimer, the term of this patent is extended or adjusted under 35 U.S.C. 154(b) by 1063 days.

(21) Appl. No.: 17/251,094

(22) PCT Filed: Jun. 20, 2019

(86) PCT No.: PCT/US2019/038277
§ 371 (c)(1),
(2) Date: Dec. 10, 2020

(87) PCT Pub. No.: WO2019/246416
PCT Pub. Date: Dec. 26, 2019

(65) Prior Publication Data
US 2021/0128785 A1 May 6, 2021

Related U.S. Application Data

(60) Provisional application No. 62/688,141, filed on Jun. 21, 2018.

(51) Int. Cl.
*A61L 27/36* (2006.01)
*A61F 2/02* (2006.01)
(Continued)

(52) U.S. Cl.
CPC .......... *A61L 27/3625* (2013.01); *A61F 2/022* (2013.01); *A61K 35/36* (2013.01);
(Continued)

(58) Field of Classification Search
CPC ..................................... A61L 27/507
See application file for complete search history.

(56) References Cited

U.S. PATENT DOCUMENTS 4,546,500 A * 10/1985 Bell .......................... A61F 2/06
623/921
5,370,681 A * 12/1994 Herweck ................. A61L 27/56
623/1.48
(Continued)

FOREIGN PATENT DOCUMENTS

CN  103756955 A  4/2014
CN  103767804 A  5/2014
(Continued)

OTHER PUBLICATIONS

International Search Report and Written Opinion for international application No. PCT/US2019/038277, issued on Oct. 2, 2019.
(Continued)

*Primary Examiner* — Thaddeus B Cox
(74) *Attorney, Agent, or Firm* — Saul Ewing LLP; Justin Crotty; Kathryn Doyle

(57) ABSTRACT

The present invention provides compositions, systems and methods for treating diabetes in a subject. The composition of the present invention includes a decellularized vascular graft, a biocompatible hydrogel encasement with tunable rigidity, and a plurality of cells such as pancreatic islet cells.

7 Claims, 26 Drawing Sheets

(51) Int. Cl.
  *A61K 35/36*   (2015.01)
  *A61K 35/545*  (2015.01)
  *A61L 27/34*   (2006.01)
  *A61L 27/38*   (2006.01)
  *A61L 27/52*   (2006.01)
  *A61L 27/54*   (2006.01)

(52) U.S. Cl.
  CPC ............ *A61K 35/545* (2013.01); *A61L 27/34* (2013.01); *A61L 27/3834* (2013.01); *A61L 27/52* (2013.01); *A61L 27/54* (2013.01); *A61L 2300/43* (2013.01)

(56) References Cited

U.S. PATENT DOCUMENTS

| | | | |
|---|---|---|---|
| 10,188,499 B2 | 1/2019 | Winkler et al. | |
| 2002/0142458 A1 | 10/2002 | Williams et al. | |
| 2005/0209687 A1* | 9/2005 | Sitzmann | C12M 25/14 623/1.41 |
| 2007/0254005 A1 | 11/2007 | Pathak et al. | |
| 2011/0276125 A1* | 11/2011 | Walker | G03F 7/24 430/320 |
| 2014/0017304 A1 | 1/2014 | Bosmans et al. | |
| 2015/0094797 A1* | 4/2015 | Matheny | A61L 27/38 623/1.46 |
| 2015/0166962 A1 | 6/2015 | Gerecht et al. | |
| 2016/0030638 A1 | 2/2016 | Ross | |
| 2016/0058913 A1 | 3/2016 | Dimitrievska et al. | |
| 2016/0287756 A1 | 10/2016 | Lewis et al. | |
| 2017/0007391 A1 | 1/2017 | Inoue | |
| 2018/0085492 A1 | 3/2018 | Ameer et al. | |
| 2020/0078160 A1* | 3/2020 | Magin | A61L 27/24 |

FOREIGN PATENT DOCUMENTS

| | | |
|---|---|---|
| CN | 106163581 A | 11/2016 |
| EP | 3810032 A4 | 4/2022 |
| JP | H04-292169 A | 10/1992 |
| JP | 2014-509617 A | 4/2014 |
| JP | 2016530899 A | 10/2016 |
| JP | 2017018330 A | 1/2017 |
| JP | 2018123934 A | 8/2018 |
| WO | 2017136786 A1 | 8/2017 |
| WO | 2018055452 A1 | 3/2018 |
| WO | 2019246416 A1 | 12/2019 |

OTHER PUBLICATIONS

Lin, et al. "In vivo performance of decellularized vascular grafts: a review article." International journal of molecular sciences 19.7 (2018): 2101.

Extended European Search Report for European Application No. 19822304.2, issued on Mar. 7, 2022.

* cited by examiner

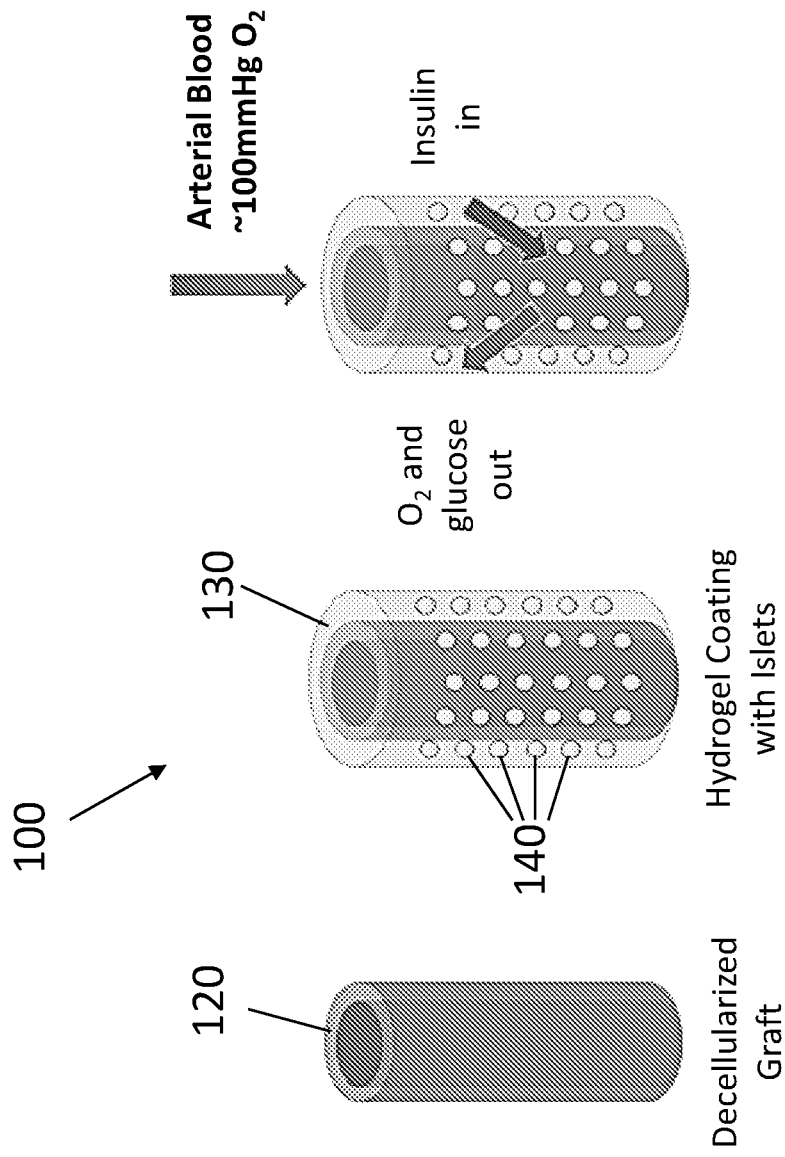

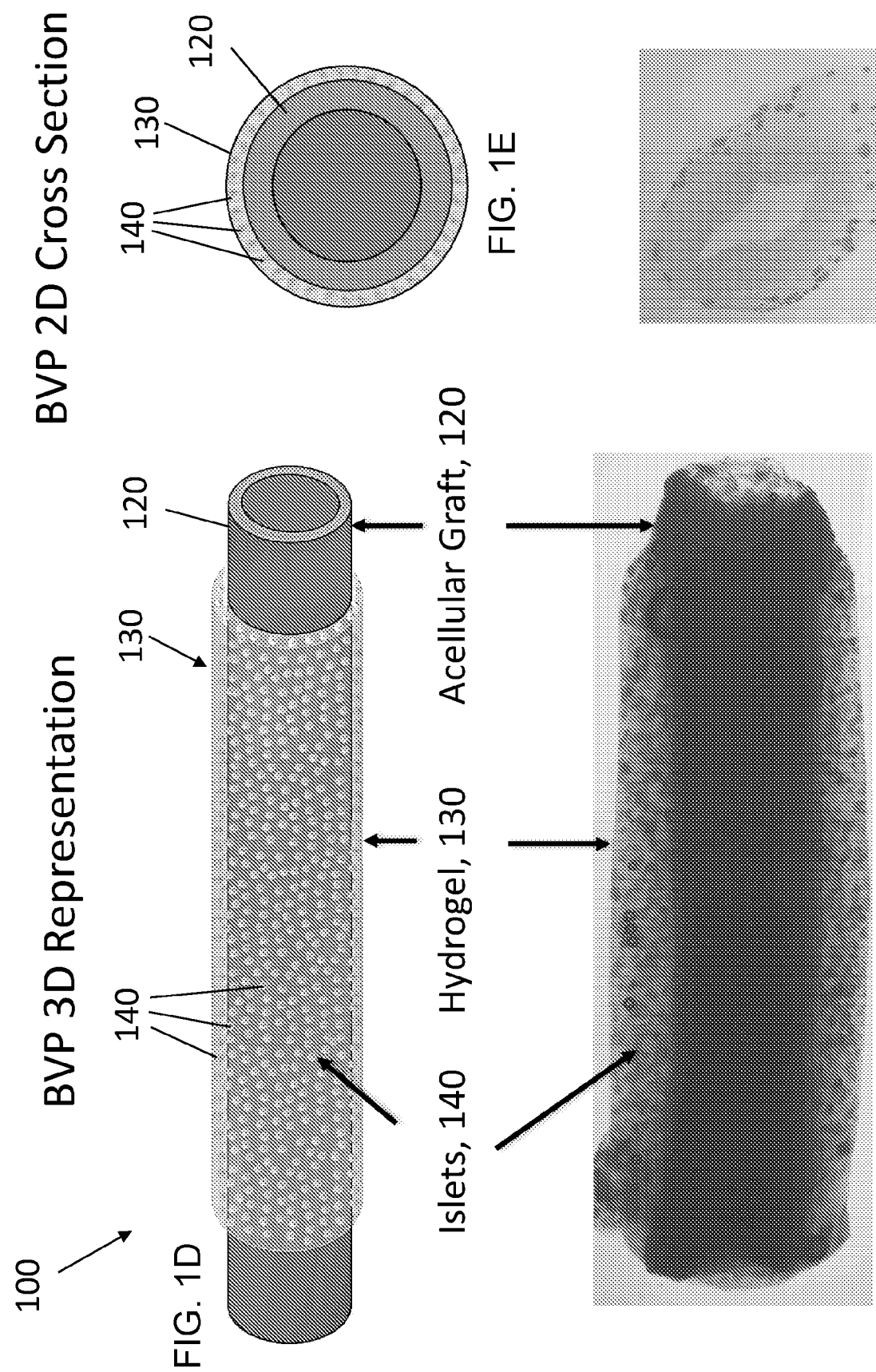

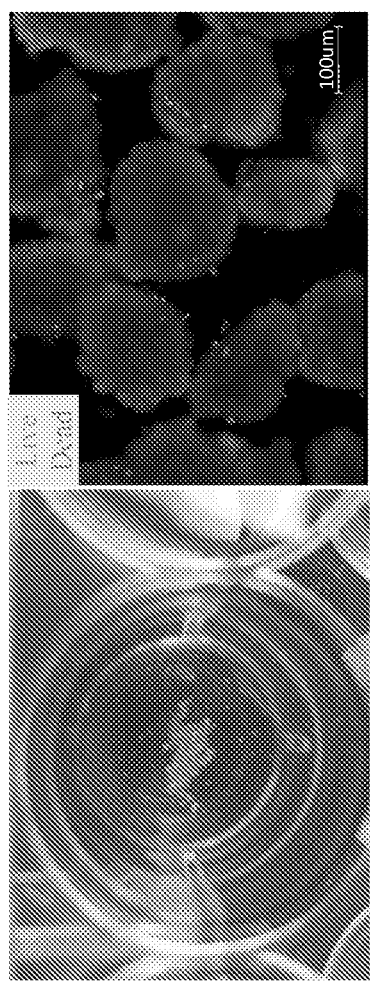

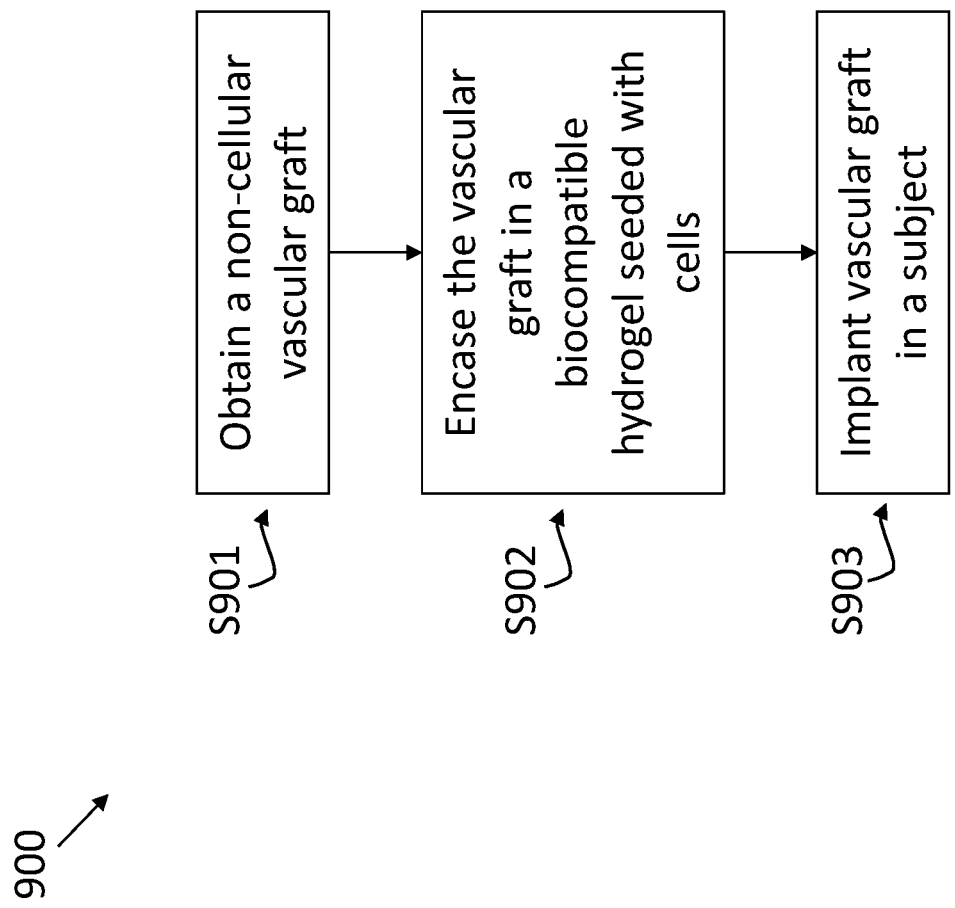

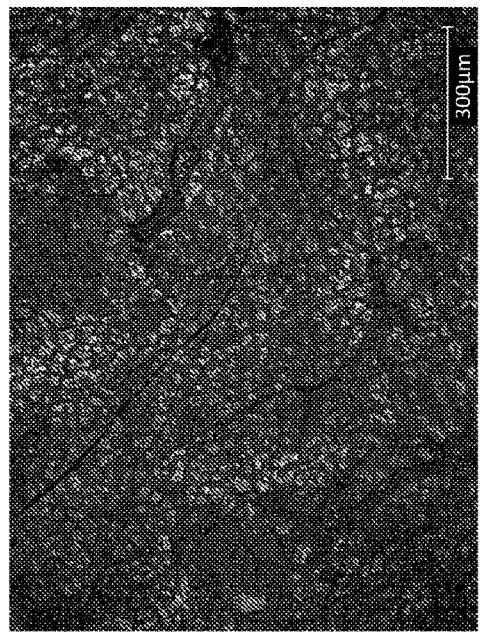
FIG. 17B
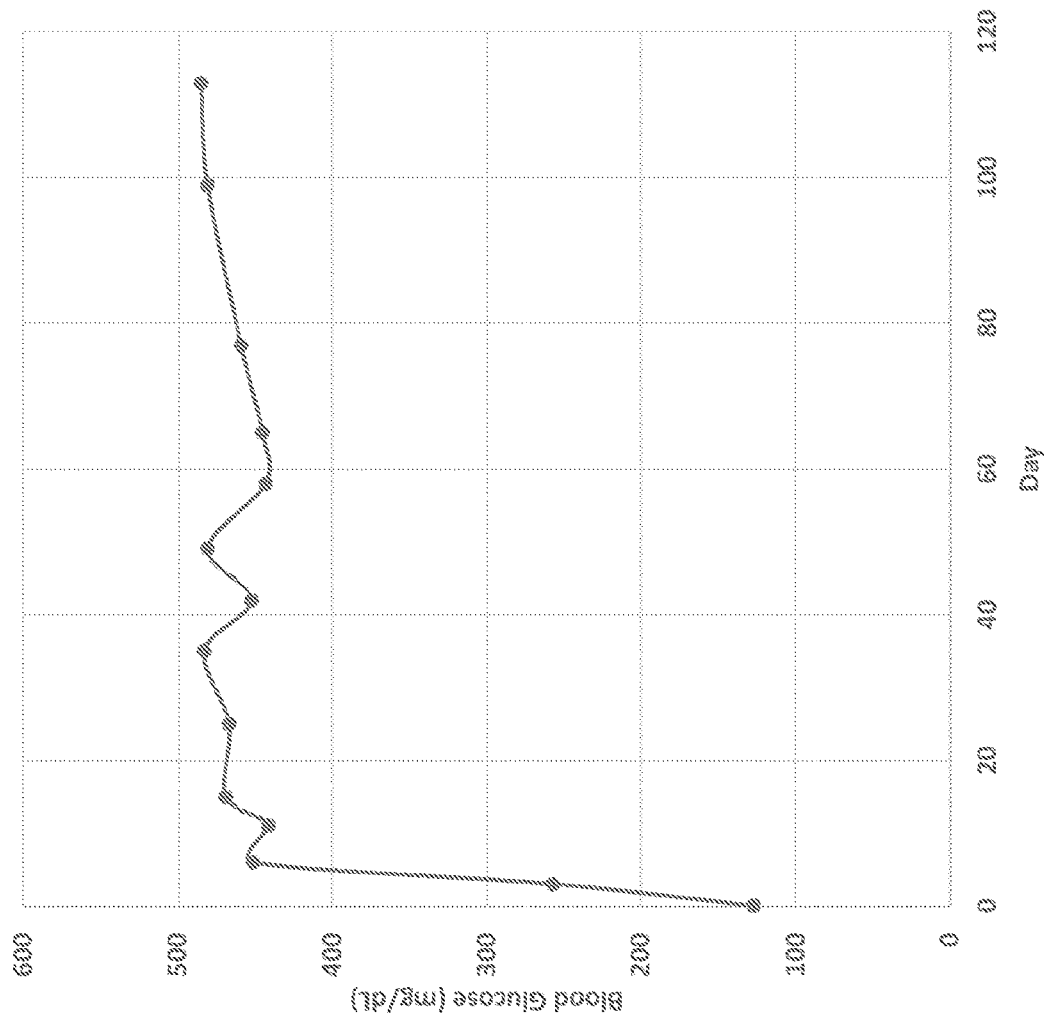
FIG. 17A

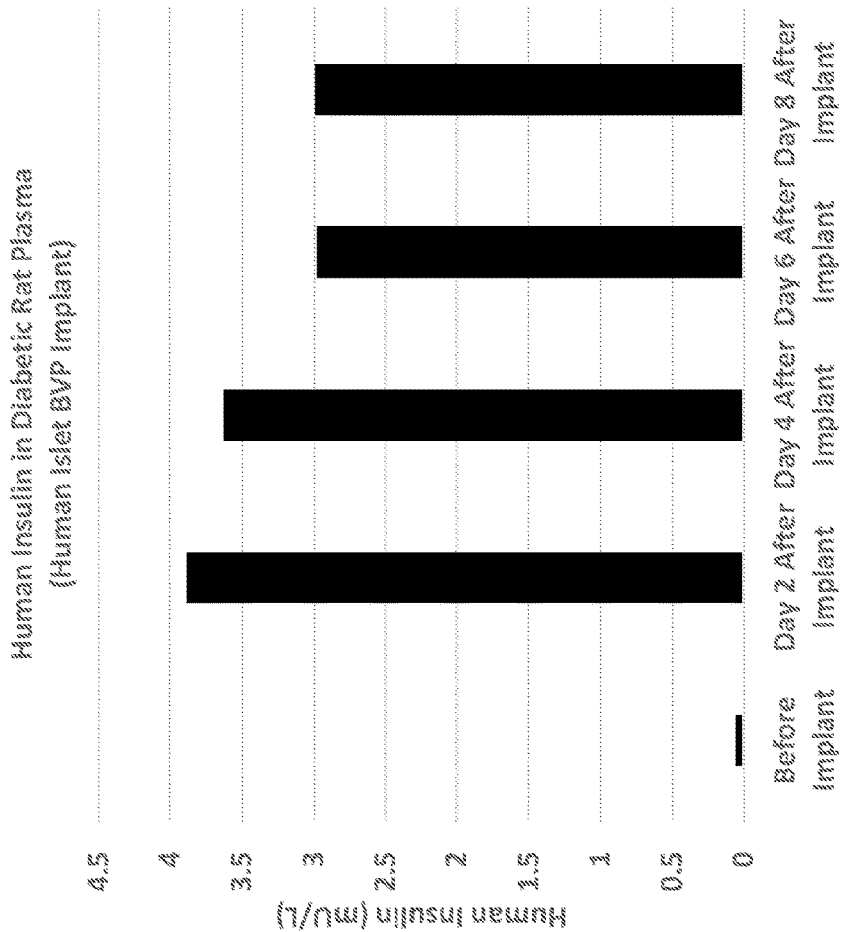
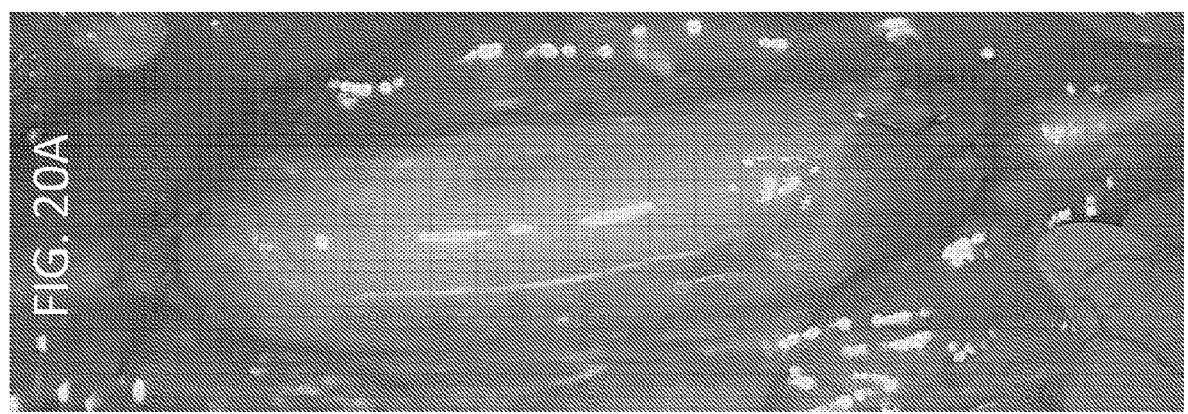
FIG. 20A
FIG. 20B

BIOARTIFICIAL VASCULAR PANCREAS

CROSS-REFERENCE TO RELATED APPLICATIONS

This application is a 35 U.S.C. § 371 national phase application from, and claiming priority to, International Application No. PCT/US2019/038277, filed Jun. 20, 2019, which claims benefit of priority under 35 U.S.C. § 119(e) to U.S. Provisional Patent Application No. 62/688,141, filed Jun. 21, 2018, which are hereby incorporated by reference in their entireties herein.

STATEMENT REGARDING FEDERALLY SPONSORED RESEARCH OR DEVELOPMENT

This invention was made with government support under HL127386, awarded by the National Institutes of Health (NIH). The government has certain rights in the invention.

BACKGROUND OF THE INVENTION

Transplantation of pancreatic islet cells can restore endocrine control of blood sugar levels, and provides patients with improved glycemic control to avoid the debilitating side effects of Type I diabetes. Currently, the only clinically utilized islet therapy is the Edmonton Protocol, which involves isolating islets from donor pancreases and injecting them into the portal vein of the recipient (Shapiro et al. NEJM 2006, 355: 1318-1330; Jin and Kim, Korean J of Int Med 2017, 32:62-66). The islets then take residence in the vascular structures of the liver, where they can sense glucose levels and secrete insulin accordingly (Korsgren et al., Diabetologia 2008, 51: 227-32; Shapiro et al., Nat Rev Endocrinol 2017, 13:268-277). Unfortunately, islet transplantation success is not guaranteed, since many transplanted islets will fail to engraft because they do not receive adequate oxygenation and nutrients (Bruni et al., Diabetes, Metabolic Syndrome and Obesity: Targets and Therapy 2014, 7:211-223.; Narang et al., Pharm Res 2004, 21: 15-25; Pepper et al., World Journal of Transplantation 2013, 3: 48-53). As such, multiple donor pancreases are often required for a single recipient, which taxes the availability of organs for transplantation.

Other islet delivery therapies being developed, such as islet microencapsulation to protect from recipient immune response, also suffer from issues relating to islet hypoxia and inadequate nutrient transfer after subcutaneous or intraperitoneal transplantation (Pepper et al., Clinical and Developmental Immunology 2013, 2013:13; Barkai et al., World Journal of Transplantation 2016, 6: 69-90; Qi et al., Biomaterials 2010, 31: 4026-4031; Coronel and Stabler, Curr Opin Biotechnol 2013, 24: 900-8). For these reasons, immune isolation of transplanted pancreatic islets has not progressed to clinical implementation despite three to four decades of research in this area.

SUMMARY OF THE INVENTION

The present invention provides a composition comprising a decellularized vascular graft, a biocompatible hydrogel encasement with tunable rigidity, and a plurality of cells. In some embodiments, the decellularized vascular graft comprises a decellularized arterial graft. In some embodiments, the decellularized vascular graft comprises a decellularized venous graft. In some embodiments, the decellularized vascular graft comprises an engineered vascular graft. In some embodiments, the hydrogel encasement comprises fibrin, fibrinogen, thrombin, collagen, elastin, gelatin, chitosans, Matrigel®, alginate, laminin, hyaluronans, silk, polyethylene glycol, isolated extracellular matrix hydrogels, or combinations thereof. In some embodiments, the plurality of cells are pancreatic islet cells. In some embodiments, the plurality of cells are seeded within the hydrogel encasement. In some embodiments, the plurality of cells are seeded on the surface of the hydrogel encasement. In some embodiments, the pancreatic islet cells are mammalian pancreatic islet cells selected from the group consisting of bovine, porcine, murine, rattus, equine, and human islet cells.

The present invention also provides a culture system that includes a biocompatible substrate with tunable rigidity, wherein said biocompatible substrate comprises a decellularized vascular graft; and a hydrogel encasement. In some embodiments, the hydrogel encasement comprises a plurality of cells. In some embodiments, the plurality of cells comprises pancreatic islet cells. In some embodiments, the plurality of islet cells are mammalian cells, selected from the group consisting of: bovine, porcine, murine, rattus, equine, and human islet cells. In some embodiments, the hydrogel encasement comprises fibrin, fibrinogen, thrombin, or combinations thereof.

The present invention also provides a method of treating diabetes in a patient, comprising, encasing a non-cellular vascular graft in a biocompatible hydrogel; wherein the biocompatible hydrogel is seeded with cells, and implanting the vascular graft into a subject. In some embodiments, the vascular graft comprises an arterial vascular graft. In some embodiments, the vascular graft comprises a venous vascular graft. In some embodiments, the biocompatible hydrogel comprises fibrin, fibrinogen, thrombin, or combinations thereof. In some embodiments, the cells include pancreatic islet cells. In some embodiments, the subject is a human subject.

BRIEF DESCRIPTION OF THE DRAWINGS

The following detailed description of preferred embodiments of the invention will be better understood when read in conjunction with the appended drawings wherein like reference characters denote corresponding parts throughout the several views. For the purpose of illustrating the invention, there are shown in the drawings embodiments which are exemplified. It should be understood, however, that the invention is not limited to the precise arrangements and instrumentalities of the embodiments shown in the drawings.

FIGS. 1A-1E depict schematics of an exemplary bioartificial vascular pancreas (BVP) of the present invention. The concept for the BVP involves constructing an islet transplantation platform that can be directly integrated with the bloodstream of the patient. For the BVP, a decellularized vascular graft (FIG. 1A) is used as a starting scaffold. The graft is then coated with islets using a hydrogel (FIGS. 1B, 1D). After implanting the BVP into a patient, fully oxygenated arterial blood may flow through the construct (FIG. 1C). This allows for oxygen and glucose to diffuse from the bloodstream out to the islets and the insulin secreted from the islets to diffuse into the bloodstream. FIG. 1E depicts a two-dimensional cross-section of the BVP. FIG. 1F depicts a light microscopy image of an exemplary BVP. FIG. 1G depicts hematoxylin and eosin (H&E) staining of a cross-section of an exemplary BVP.

FIG. 2A and FIG. 2B depict images of rat islets. FIG. 2A illustrates freshly isolated rat islets and FIG. 2B illustrates islets stained using FDA/PI, green indicates live cells while red indicates dead cells. The majority of islets are green and survive the isolation process.

FIG. 4A illustrates a metal syringe that is inserted into the lumen of a decellularized vessel. FIG. 4B depicts the vessel transferred into a 1 mL syringe containing fibrin and islets. FIG. 4C depicts the hydrogel allowed to solidify around the decellularized vessel and that the fully coated BVP is then extracted from the plastic syringe. FIG. 4D depicts a series of panels demonstrating the molding process for creating a BVP using a syringe, including a panel illustrating the BVP removed from the syringe. FIG. 4E depicts H&E staining of a cross section of an exemplary BVP. FIG. 4F depicts dithizone staining of a BVP which turns pancreatic islets (dark circles). FIG. 4G depicts live/dead staining to show islet viability after the BVP creation process using fluorescein diacetate (Sigma) and propidium iodide (Invitrogen).

FIG. 6, row A illustrates fluorescein diacetate/propidium iodide (FDA/PI) which stains live cells green and dead cells red. Results showed that the majority of cells are green and alive. FIG. 6, row B illustrates TUNEL staining which stains dead nuclei green while DAPI stains nuclei blue. Since the majority of nuclei are not green, the majority of cells survived in the fibrin gels.

FIG. 7A illustrates islets in fibrin in an exemplary transwell setup. FIG. 7B provides insulin release data. Islets were cultured inside fibrin in a transwell setup. An image of the islets in fibrin (left). Media surrounding the islet/fibrin transwell was sampled in order to test for the presence of insulin. Insulin levels tracked over time show create a slope of 23.8 pg/islet/min which shows that the islets are releasing 23 pg insulin per islet per minute which is close to the accepted literature value of 20 pg per islet per minute.

FIG. 9A depicts H&E staining showing nuclei in dark blue to identify cells and proteins in pink to identify proteins. The innermost circle is the circular cross section of the decellularized vessel while the outer dark dotted layer is the fibrin coating containing MIN6 cells. FIG. 9B depicts a close-up image of the MIN6+fibrin outer layer. FIG. 9C depicts DAPI/TUNEL staining of a cross section. TUNEL stains dead nuclei green while DAPI stains all nuclei blue. From the image, the outer ring of MIN6 cells surrounding the decellularized vessel can be seen and the majority of the cells are alive. This bioreactor setup demonstrates that the BVP setup is capable of supporting cell survival.

FIG. 10A depicts the BVP immediately after implantation inside the dotted circle. FIG. 10B depicts the BVP after 2 weeks inside the rat, highlighted inside the dotted circle. Microvessel in-growth on the BVP was observed as indicted by the arrows. The graft remained patent for the entire experiment.

FIG. 11A illustrates that the vessels remained patent but did have some thrombus in the lumen. FIG. 11B, depicts a zoomed-in picture showing surviving islets inside the fibrin coating, after 2 weeks in vivo.

FIG. 14 depicts an exemplary method of the present invention.

FIG. 17A depicts the blood glucose levels in rats treated with streptozotocin to induce diabetes. Results demonstrate the effect of the use of the drug streptozotocin at a concentration of 65 mg/kg to induce diabetes in rats and cause prolonged hyperglycemia. FIG. 17B illustrates immunofluorescent staining showing the destruction of pancreatic islets after streptozotocin injection. The upper panel depicts insulin, highlighted by the arrows, whereas the lower panel showing staining of an exemplary pancreatic islet of a treated rat has no insulin staining.

FIG. 20A illustrates a BVP constructed using 1200 human islets and transplanted into a diabetic rat. Human insulin is detected in the rat plasma after transplanting the human islet, shown in FIG. 20B.

DETAILED DESCRIPTION OF THE INVENTION

Definitions

Figure 3:
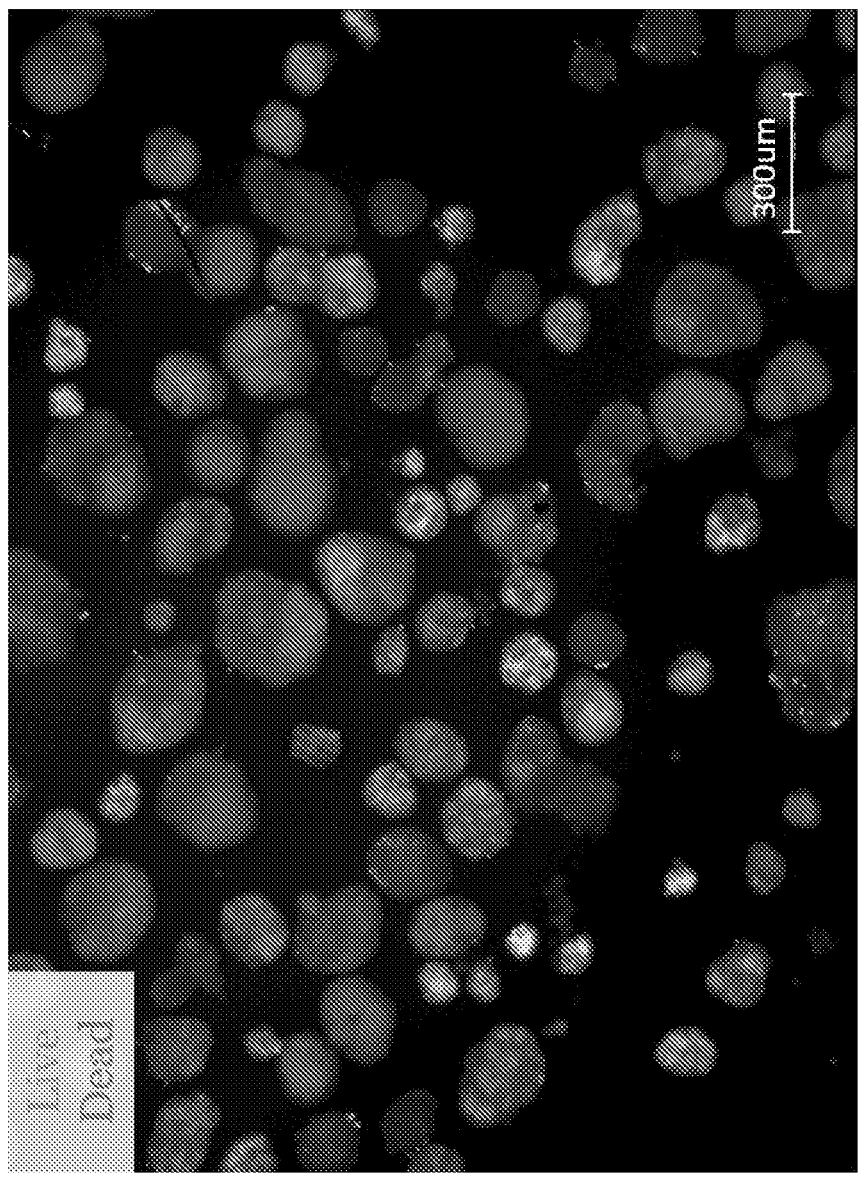
FIG. 3 depicts images of porcine islets. Isolated porcine islets stained using FDA/PI, green indicates live cells while red indicates dead cells. The majority of islets are green and survive the isolation process.
Figure 4C:
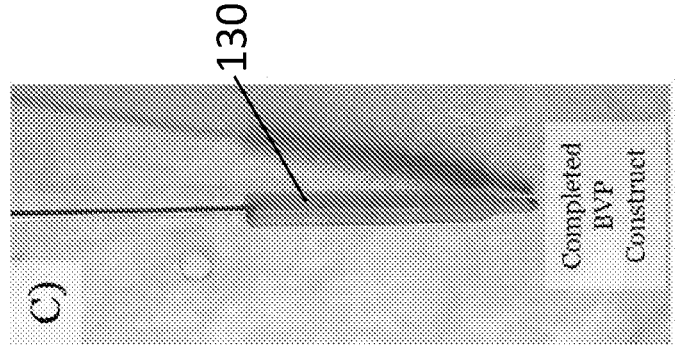
FIGS. 4A-4G illustrate an exemplary fibrin coating process. The BVP is created using a molding process to coat a decellularized vessel with fibrin/islets.
Figure 4B:
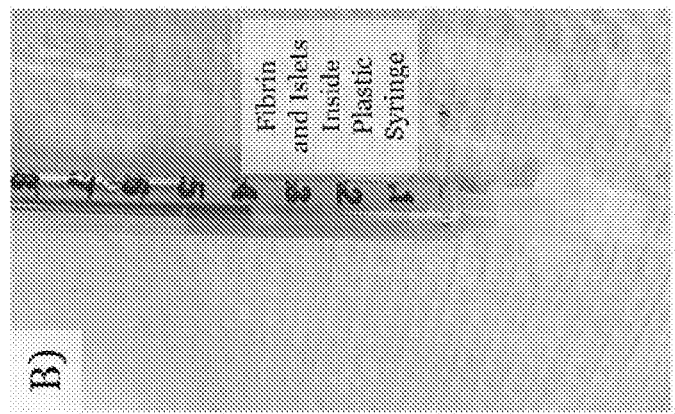
Figure 4A:
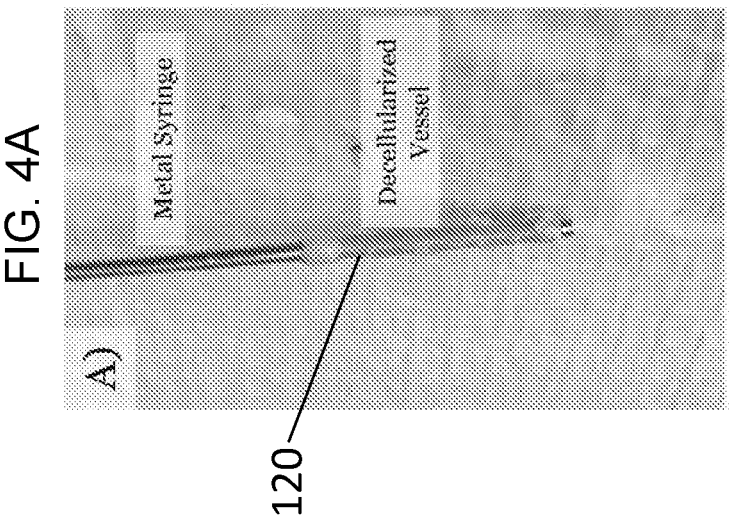
Figure 4D:
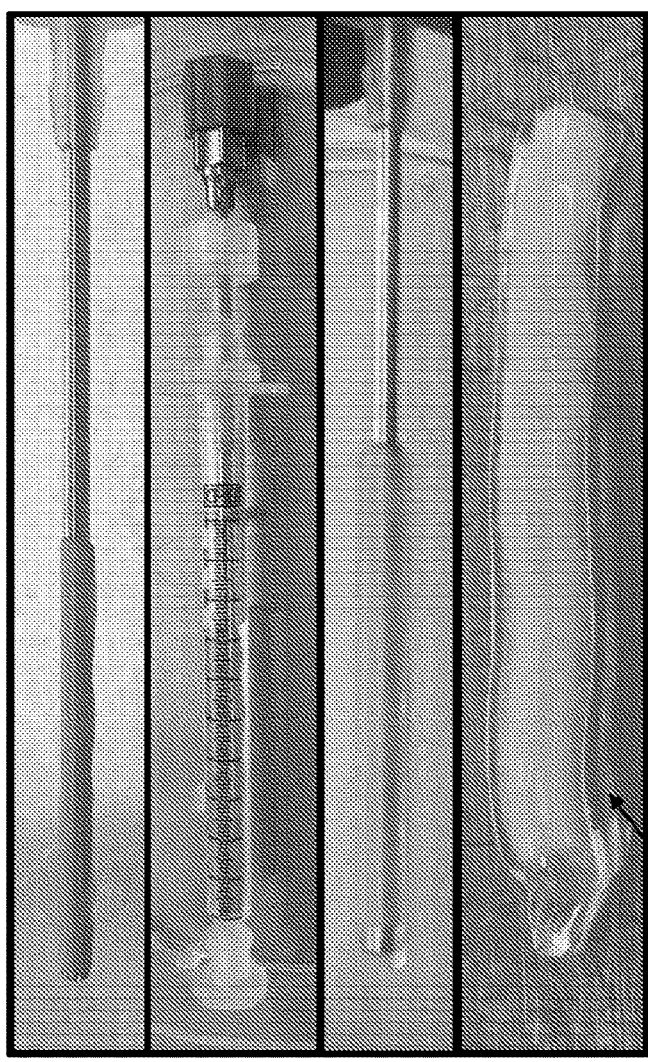
Figure 4E:
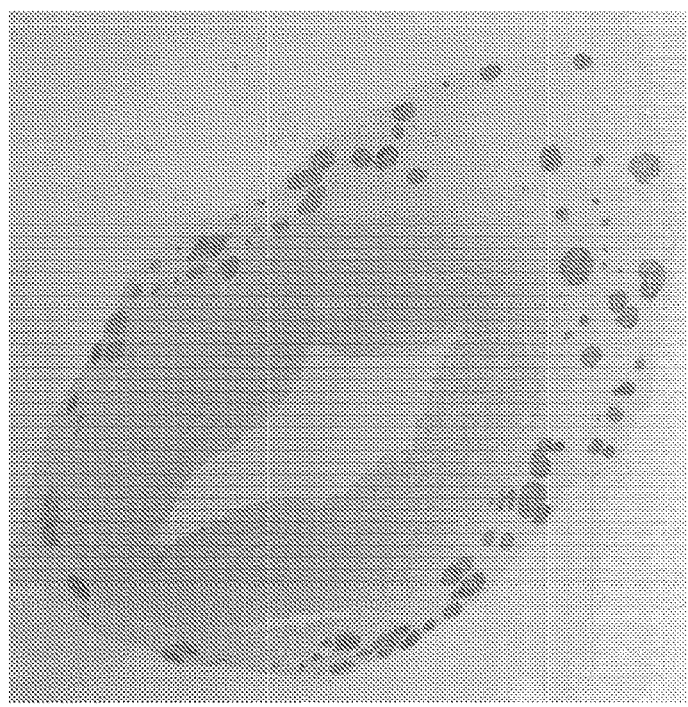
Figure 4G:
Figure 4F:
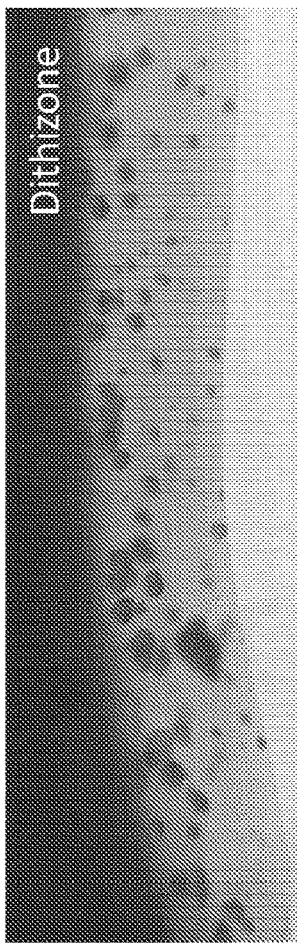

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used in the specification and claims, the terms "comprises," "comprising," "containing," "having," and the like can have the meaning ascribed to them in U.S. patent law and can mean "includes," "including," and the like.

As used herein, to "alleviate" a disease, defect, disorder or condition means reducing the severity of one or more symptoms of the disease, defect, disorder or condition.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

As used here, "biocompatible" refers to any material, which, when implanted in a mammal, does not provoke a significant adverse response in the mammal. A biocompatible material, when introduced into an individual, is not toxic or injurious to that individual, nor does it induce immunological rejection of the material in the mammal.

As used herein, the terms "biocompatible polymer" and "biocompatibility" when used in relation to polymers are recognized in the art. For example, biocompatible polymers include polymers that are generally neither toxic to the host, nor degrade (if the polymer degrades) at a rate that produces monomeric or oligomeric subunits or other byproducts at toxic concentrations in the host. In one embodiment, biodegradation generally involves degradation of the polymer in a host, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in one embodiment, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

The term "decellularized" or "decellularization" as used herein refers to a biostructure (e.g., an organ, or part of an organ, or a tissue), from which the cellular content has been removed leaving behind an intact acellular infra-structure. Some organs are composed of various specialized tissues.

The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue cells, leaving behind the complex three-dimensional network of extracellular matrix. The connective tissue infra-structure is primarily composed of collagen. The decellularized structure provides a biocompatible substrate onto which different cell populations can be infused. Decellularized biostructures can be rigid, or semi-rigid, having an ability to alter their shapes.

The term "derived from" is used herein to mean to originate from a specified source.

As used herein, "extracellular matrix composition" includes both soluble and non-soluble fractions or any portion thereof. The non-soluble fraction includes those secreted extracellular matrix (ECM) proteins and biological components that are deposited on the support or scaffold. The soluble fraction refers to culture media in which cells have been cultured and to cell secreted active agent(s) and including those proteins and biological components not deposited on the scaffold. Both fractions may be collected, and optionally further processed, and used individually or in combination in a variety of applications as described herein.

As used herein, the term "gel" refers to a three-dimensional polymeric structure that itself is insoluble in a particular liquid but which is capable of absorbing and retaining large quantities of the liquid to form a stable, often soft and pliable, but always to one degree or another shape-retentive, structure. When the liquid is water, the gel is referred to as a hydrogel. Unless expressly stated otherwise, the term "gel" will be used throughout this application to refer both to polymeric structures that have absorbed a liquid other than water and to polymeric structures that have absorbed water, it being readily apparent to those skilled in the art from the context whether the polymeric structure is simply a "gel" or a "hydrogel."

As used herein, a "graft" refers to a composition that is implanted into an individual, typically to replace, correct or otherwise overcome a cell, tissue, or organ defect. A graft may comprise a scaffold. In certain embodiments, a graft comprises decellularized tissue. In some embodiments, the graft may comprise a cell, tissue, or organ. The graft may consist of cells or tissue that originate from the same individual; this graft is referred to herein by the following interchangeable terms: "autograft," "autologous transplant," "autologous implant" and "autologous graft." A graft comprising cells or tissue from a genetically different individual of the same species is referred to herein by the following interchangeable terms: "allograft," "allogeneic transplant," "allogeneic implant" and "allogeneic graft." A graft from an individual to his identical twin is referred to herein as an "isograft," a "syngeneic transplant," a "syngeneic implant" or a "syngeneic graft." A "xenograft," "xenogeneic transplant" or "xenogeneic implant" refers to a graft from one individual to another of a different species.

As used herein, the term "islet" refers to a pancreatic islet, which is a cluster of multiple endocrine cell types found in the pancreatic islet or islets of Langerhans of a subject. The islet may consist of a cluster of one or more cells including one or more alpha cells, beta cells, delta cells, PP cells, epsilon cells, and in some cases, some portion of surrounding tissue including connective tissue and extracellular matrix constituents.

As used herein, "islet cells" refers to the cells contained within a pancreatic islet, including alpha cells, beta cells, delta cells, PP cells, epsilon cells. Isolated and purified islets, as used herein, refers to islets isolated and prepared according to methods as described herein.

As used herein, the term "polymerization" or "cross-linking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combination thereof. A polymerization or cross-linking reaction may consume between about 0% and about 100% of the at least one functional group available in the system. In one embodiment, polymerization or cross-linking of at least one functional group results in about 100% consumption of the at least one functional group. In another embodiment, polymerization or cross-linking of at least one functional group results in less than about 100% consumption of the at least one functional group.

As used herein, "scaffold" refers to a structure, comprising a biocompatible material that provides a surface suitable for adherence of a substance and proliferation of cells. A scaffold may further provide mechanical stability and support. A scaffold may be in a particular shape or form so as to influence or delimit a three-dimensional shape or form such as that assumed by a population of proliferating cells. Such shapes or forms include, but are not limited to, films (e.g. a form with two-dimensions substantially greater than the third dimension), ribbons, cords, sheets, flat discs, cylinders, spheres, three-dimensional amorphous shapes, etc.

As used herein, to "treat" means reducing the frequency with which symptoms of a disease, defect, disorder, or adverse condition, and the like, are experienced by a patient.

The term "tissue," as used herein includes, but is not limited to, bone, neural tissue, fibrous connective tissue including tendons and ligaments, cartilage, dura, pericardia, muscle, lung, heart valves, veins and arteries and other vasculature, dermis, adipose tissue, or glandular tissue.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

As used herein, the term "treating a disease or disorder" means reducing the frequency with which a symptom of the disease or disorder is experienced by a patient. Disease and disorder are used interchangeably herein.

As used herein, the term "effective amount" or "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

Description

The present invention relates to compositions for the delivery of pancreatic islet cells, systems and methods for making such compositions, and methods for using such compositions. In particular, the present invention relates to systems, biomaterials, tissue engineered constructs, and the like, that are used to develop bioartificial vascular pancreas (BVP) compositions. The present invention is based on the discovery that seeding cells on decellularized vascular grafts significantly improves islet cell function and survival. In certain embodiments, the BVP compositions provide decellularized vascular grafts or other acellular or non-cellular types of arterial/vascular grafts, and biocompatible hydrogel compositions. In certain embodiments, the biocompatible hydrogel compositions are seeded with cells. In certain embodiments, cells or islets are affixed to the outside of an acellular or non-cellular vascular graft, without the use of a hydrogel carrier. In certain embodiments, islets or cells are affixed to the outside of a cellular artery, vein, or cellular vascular grafting conduit. In certain embodiments, the present invention provides systems for culturing pancreatic islet cells. In certain embodiments, the present invention provides methods for treating diseases of the pancreas (e.g., type I or type II diabetes) in a subject.

BVP Compositions

Referring now to FIGS. 1A-1G, the BVP 100 of the present invention comprises one or more decellularized vascular grafts 120 (FIG. 1A). In some embodiments, the decellularized vascular graft 120 is a decellularized arterial vascular graft wherein the arterial graft is isolated from an arterial blood vessel such as, for example, an umbilical artery, aorta, abdominal aorta, thoracic aorta, mammary artery, brachial artery, radial artery, gastro-epiploic artery, inferior epigastric artery, splenic artery, subscapular artery, inferior mesenteric artery, descending branch of the lateral femoral circumflex artery, ulnar artery, intercostal artery, and any other suitable arterial tissue as understood by those skilled in the art. In some embodiments, the decellularized vascular graft 120 is a decellularized venous vascular graft wherein the venous graft is isolated from a venous blood vessel such as, for example, a saphenous vein, umbilical vein, or any other suitable venous tissue as understood by those skilled in the art. In some embodiments, the vascular graft is an autograft. In some embodiments, the vascular graft is a xenograft. In some embodiments, the vascular graft is an allograft. In some embodiments, the decellularized vascular graft is a decellularized engineered vascular graft. In some embodiments, the engineered vascular graft is an engineered arteriovenous graft. Engineered grafts may be constructed using any technique as understood in the art, including but not limited to: decellularization, cell self-assembly, electrospinning, phase separation, and the like. In some embodiments, the vascular graft contains cells that are living.

The one or more vascular grafts as described herein are decellularized using standard techniques as understood in the art. In one embodiment, the decellularized tissue of the invention consists essentially of the extracellular matrix (ECM) component of all or most regions of the tissue. ECM components can include any or all of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. Successful decellularization is defined as the absence of detectable endothelial cells, smooth muscle cells, epithelial cells, and nuclei in histologic sections using standard histological staining procedures. Preferably, but not necessarily, residual cell debris also has been removed from the decellularized tissue.

In some embodiments, the decellularization process of a natural tissue preserves the native three-dimensional structure of the tissue. That is, the morphology and the architecture of the tissue, including ECM components are maintained during and following the process of decellularization. The morphology and architecture of the ECM can be examined visually and/or histologically. For example, the basal lamina on the exterior surface of a solid organ or within the vasculature of an organ or tissue may not be removed or significantly damaged due to decellularization. In addition, the fibrils of the ECM may be similar to or significantly unchanged from that of an organ or tissue that has not been decellularized. In some embodiments, the mechanical properties of the natural tissue are not substantially impacted by the decellularization process.

In some embodiments the decellularized grafts are synthetic grafts. For example, the synthetic grafts may include on or more of Dacron® grafts, polytetrafluoroethylene grafts, polyurethane grafts, and the like.

In some embodiments, the one or more decellularized vascular grafts 120 are encased with a hydrogel coating 130 (FIGS. 1B and 1D). In some embodiments, the hydrogel coating 130 is constructed from one or more biocompatible biomolecules. In some embodiments, the hydrogel coating 130 comprises tunable rigidity. In some embodiments, the hydrogel coating 130 is pro-angiogenic.

In some embodiments, the hydrogel coating 130 is constructed from one or more biocompatible biomolecules, for example, fibrin, fibrinogen, and thrombin. In some embodiments, the hydrogel coating is constructed from any suitable biomolecule or combination of biomolecules suitable for forming a hydrogel as understood in the art, for example, collagen, fibrin, elastin, hyaluronic acid, gelatin, laminin, hyaluronans, chitosans, alginates, dextran, pectin, carrageenan, silk, Matrigel®, polylysine, gelatin, agarose, crosslinked polyethylene glycol, crosslinked synthetic polymeric hydrogel, extracellular matrix, for example isolated extracellular matrix, purified extracellular matrix, and/or decellularized extracellular matrix used to form a hydrogel, and the like, and/or combinations thereof (see Hennink and C. F. van Nostrum, 2002, Adv. Drug Del. Rev. 54, 13-36 and Hoffman, 2002, Adv. Drug Del. Rev. 43, 3-12). These materials consist of high-molecular weight backbone chains made of linear or branched polysaccharides or polypeptides. Examples of hydrogels based on synthetic polymers include but are not limited to (meth)acrylate-oligolactide-PEO-oligolactide-(meth)acrylate, poly(ethylene glycol) (PEO), poly (propylene glycol) (PPO), PEO-PPO-PEO copolymers (Pluronics), poly(phosphazene), poly(methacrylates), poly (N-vinylpyrrolidone), PL(G)A-PEO-PL(G)A copolymers, poly(ethylene imine), etc. (see A. S Hoffman, 2002, Adv. Drug Del. Rev, 43, 3-12). In some embodiments, the hydrogel is generated using digested decellularized pancreatic tissue. In some embodiments, the hydrogel is created using digested decellularized pancreatic tissue in combination with one or more other hydrogels, for example fibrin hydrogels. In some embodiments, the hydrogel coating 130 is constructed of a fibrous scaffold instead of a hydrogel. For example, the fibrous scaffold may include one or more of polyglycolic acid (PGA), polylactic acid, polydioxanone, caprolactone, and the like, and/or combinations thereof. In some embodiments the hydrogel coating 130 is constructed of a combination of hydrogel and non-hydrogel scaffold materials, as described herein.

In some embodiments, the hydrogel coating 130 of the present invention is mechanically stable. In some embodiments the hydrogel coating of the present invention comprises tunable mechanical properties, for example tunable rigidity. In some embodiments, the mechanical properties of the hydrogel coating are tunable by modifying the concentration of the one or more biomolecule used to form the hydrogel coating. For example, in some embodiments, the hydrogel is a fibrin hydrogel coating that is formed using varying concentrations of fibrinogen and/or thrombin. In some embodiments, the fibrin hydrogel coating is formed using varying ratios of fibrinogen with thrombin. In some embodiments, the ratio of fibrinogen to thrombin is 10:1. In some embodiments, the ratio of fibrinogen to thrombin is about 2:1, about 3:1, about 4:1 about 5:1, about 6:1, about 7:1, about 8:1, about 9:1 about 10:1, about 11:1, about 12:1, about 13:1, about 14:1, about 15:1, about 16:1, about 17:1 about 18:1, about 19:1 or about 20:1. In some embodiments, the fibrin hydrogel coating is formed using a fibrinogen concentration of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 15 mg/mL, or about 20 mg/mL. In some embodiments, the fibrin hydrogel coating is formed using a fibrinogen concentration of about 5 mg/mL in a 5:1 ratio with thrombin. In some embodiments, the fibrin hydrogel coating is formed using a fibrinogen concentration of about 10 mg/mL in a 5:1 ratio with thrombin. In some embodiments, the fibrin hydrogel coating is formed using a fibrinogen concentration of about 10 mg/mL in about a 10:1 ratio with thrombin.

In some embodiments, the hydrogel coating 130 is proangiogenic. In some embodiments, the hydrogel coating is constructed from biocompatible biomolecules that support angiogenesis. The term "angiogenesis", as used herein, is defined as the formation of new blood vessels from preexisting vessels. In some embodiments, the hydrogel coating of the present invention is constructed from one or more biomolecules, for example fibrin, that support the ingrowth of new blood vessels. In some embodiments, the hydrogel coating is constructed from one or more biomolecules that support blood vessel maturation and/or stability. In some embodiments, the hydrogel coating comprises one or more angiogenic factors, for example vascular endothelial growth factor (VEGF), fibroblast growth factor (FGF), platelet-derived growth factor (PDGF), angiopoeitins (Ang-1, Ang-2), transforming growth factor (TGF-β), and the like. In some embodiments, one or more factors are combined or incorporated into the hydrogel directly. In some embodiments, one or more factors are delivered to the hydrogel by direct means, such as direct injection or direct contact. In some embodiments, one or more factors are delivered to the hydrogel using delivery methods as understood in the art, for example conjugation or encapsulation in microparticles, nanoparticles, and the like.

In some embodiments, the hydrogel coating 130 of the present invention is seeded with a plurality cells 140, as shown in FIGS. 1B and 1D. In some embodiments, the cells 140 include pancreatic islet cells. In some embodiments, the cells 140 include alpha cells, beta cells, delta cells, PP cells, and/or epsilon cells. In some embodiments, the cells 140 are intact islets, for example isolated intact islets. In some embodiments, the isolated intact islets are isolated from a mammalian source, including for example bovine, porcine, murine, and/or human islets. In some embodiments, the cells are transformed cells, for example immortalized cells such as insulinoma cells, transgenic cells, knock-out cells, knock-in cells, or otherwise genetically modified cells. In some embodiments, the cells are modified to produce and/or secrete elevated levels of insulin, proinsulin, C-peptide and the like. In some embodiments the cells are stem cells including embryonic stem cells (ESCs), induced pluripotent stem cells (IPSCs), and the like. In some embodiments the cells are progenitor cells differentiated from ESCs or IPSCs. In some embodiments, the hydrogel coating 130 is seeded with other cell types capable of secreting useful compounds. In some embodiments, these cells are exocrine cells. In some embodiments, these cells are endocrine cells. In some embodiments these endocrine cells are follicular cells, neuroendocrine cells, or parathyroid cells. In some embodiments, the seeded cells are allograft cells. In some embodiments, the seeded cells are autograft cells. In some embodiments, the seeded cells are xenograft cells.

In some embodiments, the hydrogel coating 130 is seeded with a plurality of isolated cells. In some embodiments, the hydrogel coating is seeded with a plurality of intact islets. In some embodiments, the hydrogel coating is seeded with about 25,000 cells, about 50,000 cells, about 75,000 cells, about 100,000 cells, about 500,000 cells, about 1,000,000 cells, about 10,000,000 cells, about 100,000,000 cells, about 500,000,000 cells, about 1,000,000,000 or about 10,000,000,000 cells. In some embodiments, the hydrogel coating is seeded with about 50 islets to about 100 islets, about 100 islets to about 500 islets, about 500 islets to about 1,000 islets, about 1,000 islets to about 5,000 islets, about 5,000 islets to about 10,000 islets, about 10,000 islets to about 50,000 islets, about 50,000 islets to about 100,000 islets, about 100,000 islets to about 500,000 islets, about 500,000 islets to about 1,000,000 islets, or about 1,000,000 islets to about 5,000,000 islets.

Culturing System

In certain aspects, the present invention provides a system for culturing isolated pancreatic islet cells. Pancreatic islets may be cultured after isolation using a variety of methods that are known in the art, including culture in suspension, culture in or on polystyrene dishes, culture in transwell inserts, culture in hollow-fiber flow devices, and the like. In some cases, the islets may be cultured while residing within a hydrogel. In some embodiments, the culture system includes one or more BVP compositions 100, as described herein, connected to one or more perfusion systems, for example the bioreactor system 800 shown in FIG. 8. In some embodiments, bioreactor system 800 comprises one or more elements including one or more interstitial space reservoirs 810, one or more pumps 820, and one or more lumen reservoirs 830, wherein the one or more elements are fluidly connected with one or more lengths of tubing 840.

The one or more interstitial space reservoirs 810 can be any suitable reservoir container as understood in the art for containing one or more BVPs of the present invention with suitable conditions. In some embodiments, the reservoir container includes one or more ports for fluidly connecting the lumen of one or more BVPs to perfusate. In some embodiments, an interior component of the one or more ports fluidly connects to each end of the one or more BVPs on the interior of reservoir 810. In some embodiments, and exterior component of the one or more ports fluidly connects to the one or more lengths of tubing 840 on the exterior of reservoir 810. The one or more ports can include any suitable connectors or fittings as understood in the art, for examples slip fittings, barbed fittings, threaded fittings, other friction-based fittings, and the like. In some embodiments, the one or more BVPs are secured or fastened to the one or more ports using techniques such as suturing, and the like.

In some embodiments, the ports may be constructed from any suitable sterilizable biocompatible material, including glass and/or plastic. In some embodiments the ports are formed from the same material as the reservoir 810. For example, in some embodiments, the ports are extruded from the sample unit of material as the reservoir. In some embodiments, the ports are separate units of materials that are attached to the reservoir 810. Interstitial space reservoirs 810 may be constructed from any suitable sterilizable, biocompatible material as understood in the art including glass and/or plastic. In some embodiments, interstitial space reservoir 810 includes one or more sensing probes, for example oxygen sensing probes, ammonia sensing probes, and the like. In some embodiments, interstitial space reservoir 810 includes one or more sampling ports for collecting fluids from inside of the reservoir or for injecting one or more additional factors such as proteins or glucose into the reservoir. In some embodiments, interstitial space reservoir 810 includes one or more components for regulating the oxygen level inside reservoir 810. For example, in some embodiments, interstitial space reservoir includes one or more conduits for sparging reservoir 810. In some embodiments, interstitial space reservoir includes one or more conduits for degassing reservoir 810. The interstitial space may contain flowing or perfusing fluids or culture medium. The interstitial space may contain one or more sensors for measuring pressure, oxygen, glucose levels, ammonia levels, and the like.

The one or more pumps 820 may be any suitable pump for generating fluid flow, as understood in the art. For example, the one or more pumps 820 can be one or more peristaltic pumps, as understood in the art. In some embodiments, pump 820 may be one or more suitable positive displacement pumps, impulse pumps, velocity pumps, gravity pumps, steam pumps or valveless pumps, as understood by one skilled in the art.

The one or more lumen reservoirs 830 can be any suitable reservoir container, as understood in the art, for suitably containing perfusate with preferred oxygen and glucose concentrations. Lumen reservoir 830 may have one more ports, holes, or connections including, for example, ports, holes or connections for supplying air, oxygen, glucose, proteins, and the like to and/or from the perfusate, for depressurizing and/or ventilating reservoir 830, and/or for receiving one or more lengths of tubing 840. Lumen reservoir 830 may be constructed from any suitable sterilizable, biocompatible material as understood in the art.

The one or more lengths of tubing 840 as described herein can be any suitable biocompatible, sterilizable tubing as understood in the art. For example, tubing 840 may be silicone tubing, TYGON® tubing, MASTERFLEX® tubing, polyetheretherketone, or any other suitable biocompatible, sterilizable, thermoplastic elastomer tubing, as understood in the art In some embodiments, the tubing has an inner diameter of about 0.03 mm, 0.06 mm, 0.12 mm, 0.19 mm, 0.25 mm, or 0.31 mm. Bioreactor system 800 as described herein can be used to simulate the environmental conditions of an implanted BVP composition. For example, in some embodiments, the one or more lumen reservoirs 830 contain perfusate 832 wherein the perfusate 832 includes media formulated with high oxygen and glucose levels. In some embodiments, the media is any suitable cell culture basal media, as understood in the art, for example Roswell Park Memorial Institute media (RPMI), Dulbecco's modified eagle media (DMEM), media 199 (M199), or the like. In some embodiments, the perfusate 832 includes glucose and oxygen conditions similar to the conditions of blood perfusing an implanted BVP composition 100. For example, in some embodiments, perfusate 832 contains about 450 mg/dL of glucose. In some embodiments, perfusate 832 contains about 100 mg/dL, about 200 mg/dL, about 300 mg/dL, about 350 mg/dL, about 400 mg/dL, about 450 mg/dL, about 500 mg/dL, about 550 mg/dL, or about 600 mg/dL of glucose. In some embodiments perfusate 832 contains about 100 mmHg oxygen. In some embodiments, perfusate 832 contains about 40 mmHg, about 60 mmHg, about 80 mmHg, about 90 mmHg about 100 mmHg, about 110 mmHg, about 130 mmHg, about 150 mmHg, about 170 mmHg, or about 190 mmHg.

In some embodiments, the interstitial space reservoir 810 contains media 812 with low oxygen and glucose levels. In some embodiments, the media 812 includes conditions similar to the conditions in the tissue microenvironment where a BVP composition 100 is implanted. For example, in some embodiments, media 812 contains about 20 mg/dL of glucose. In some embodiments, media 812 contains at least 10 mg/dL of glucose, for example, in some embodiments, media 812 contains about 12 mg/dL, about 15 mg/dL, about 20 mg/dL, about 22 mg/dL, about 25 mg/dL, about 30 mg/dL, about 35 mg/dL, about 40 mg/dL, about 45 mg/dL, about 50 mg/dL, about 55 mg/dL, about 60 mg/dL, about 65 mg/dL, about 70 mg/dL, about 75 mg/dL, about 80 mg/dL, about 85 mg/dL, about 90 mg/dL, about 95 mg/dL, or about 100 mg/dL of glucose. In some embodiments perfusate 812 contains about 40 mmHg oxygen. In some embodiments, perfusate 832 contains about 10 mmHg, about 20 mmHg, about 30 mmHg, about 40 mmHg about 50 mmHg, about 60 mmHg, about 80 mmHg, about 100 mmHg, about 120 mmHg, or about 140 mmHg.

In some embodiments, one or more BVPs 100 are positioned within the internal space of interstitial space reservoir 810. The external surface of BVP 100 is in direct fluid contact with media 812. BVP 100 is fluidly connected to tubing 840 such that the lumen of BVP 100 is fluidly sealed with perfusate 832. In some embodiments, perfusate 832 passes through the lumen and directly contacts the inner lumen of BVP 100.

In some embodiments, pump 840 delivers perfusate 832 through bioreactor 800. In some embodiments, perfusate 832 is pumped from lumen reservoir 830 through the lumen of BVP 100, and then returns perfusate 832 to lumen reservoir 830. In some embodiments, one or more ports of reservoir 810 fluidly seal tubing 840 to the lumen of BVP 100. The entering perfusate 832 passes through the lumen of BVP 100, is isolated from media 812, and exits through tubing 840. In some embodiments, perfusate 832 diffuses across the decellularized graft of BVP 100 towards the plurality of cells 140 within hydrogel coating 130. In some embodiments, the perfusate 832 is pumped through tubing 840 at a flow rate similar to that in the pancreatic circulation. In some embodiments, perfusate 832 is pumped at a flow rate similar to that in the hepatic circulation. In some embodiments, perfusate 832 is pumped at a flow rate similar to that in arteriovenous fistulas. In some embodiments, perfusate 832 is perfused at a rate of about 1 mL/min, about 2 mL/min, about 3 mL/min, about 10 mL/min, about 50 mL/min, about 100 mL/min, or about 200 mL/min. In some embodiments, immediately after the BVP of the present invention is perfused, the plurality of cells embedded in the hydrogel encasement are immediately exposed to the oxygen and glucose content of the perfusate 832. In some embodiments, the plurality of cells are exposed to the oxygen and glucose content of the perfusate within about 5 minutes of the initiation of flow within the system. In some embodiments, the plurality of cells are exposed to the oxygen and glucose content of the perfusate within about 10 minutes or about 30 minutes of the initiation of flow within the system. The perfusate may be any suitable fluid as known and understood in the art, including buffer solution, saline solution, glucose solution, culture medium, blood, plasma, serum, and the like.

Methods

Various embodiments of the present invention provide methods for treating a disease of the pancreas, for example diabetes, including, as a non-limiting example, type I diabetes in a subject. Referring now to FIG. 14, an exemplary method 900 of treating a disease of the pancreas in a subject in need thereof is shown. In some embodiments, the disease is diabetes, including type I diabetes, type II diabetes, and the like, as described herein. Various embodiments of the present invention provide methods for delivering insulin to a subject in need thereof. Various embodiments of the present invention provide methods for delivering high volumes of cells (e.g., pancreatic islet cells) to a subject in need thereof.

In some embodiments, method 900 begins with step S901. In various embodiments, step S901 includes obtaining a decellularized, non-cellular, and/or acellular vascular graft. In various embodiments, step S901 includes decellularizing a vascular graft. In some embodiments, the vascular graft is an arterial graft. In some embodiments, the arterial graft is isolated from one or more arterial blood vessels such as, for example, an umbilical artery, aorta, abdominal aorta, thoracic aorta, mammary artery, brachial artery, radial artery, gastro-epiploic artery, inferior epigastric artery, splenic artery, subscapular artery, inferior mesenteric artery, descending branch of the lateral femoral circumflex artery, ulnar artery, intercostal artery, and any other suitable arterial tissue as understood by those skilled in the art, as described herein. In some embodiments, the vascular graft is a venous graft. In some embodiments, the venous graft is isolated from one or more venous vessels such as, for example, a saphenous vein, umbilical vein, or any other suitable venous tissue as understood by those skilled in the art, as described herein. In some embodiments, the vascular graft is an engineered vascular graft, such as an engineered non-cellular or acellular vascular graft as described herein.

In various embodiments of step S902, the decellularized vascular graft 120 is encased in a biocompatible hydrogel. Alternatively, in some embodiments, the vascular graft is not encased in a hydrogel, but rather cells are affixed to the outer surface of the graft by means such as covalent bonds, encapsulation within microparticles, or encapsulation or entrapment within extracellular matrix particles, strands, or sheets, that are tethered to or a constituent of the vascular graft. In some embodiments, the decellularized vascular graft 120 may be stabilized on a support structure in order to facilitate the encasing in hydrogel. The support structure may include a cylindrical structure appropriately sized to fit within the lumen of the graft. For example, the support structure may have a diameter of up to about 0.01 mm, about 0.01 mm to about 0.05 mm, about 0.05 mm to about 0.1 mm, about 0.1 mm to about 0.15 mm, about 0.15 mm to about 0.2 mm, about 0.2 mm to about 0.5 mm, about 0.5 mm to about 1 mm, about 1 mm to about 5 mm, about 5 mm to about 10 mm, and the like. Non-limiting examples of the support structure may include, for example, a syringe, needle, rigid and/or semi-rigid tubing or other suitable structure. The support structure may be constructed of any suitable biocompatible material including, for example, stainless steel, TYGON®, polyvinyl chloride, polycarbonate, and the like.

In some embodiments, the biocompatible hydrogel is constructed from one or more biocompatible biomolecules, for example, fibrin, fibrinogen, and thrombin. The hydrogel may be constructed from any suitable biomolecule or combination of biomolecules suitable for forming a hydrogel as understood in the art, for example, collagen, fibrin, elastin, hyaluronic acid, gelatin, laminin, alginate, other extracellular matrix proteins or constituents, and the like, as described herein. In some embodiments, the biocompatible hydrogel is mechanically stable. In some embodiments the hydrogel has tunable rigidity.

The hydrogel rigidity may be tunable by modifying the concentration of the one or more biomolecules used to form the hydrogel coating. For example, in some embodiments, the hydrogel is a fibrin hydrogel that is formed using varying concentrations of fibrinogen and/or thrombin. The fibrin hydrogel coating may be formed using varying ratios of fibrinogen with thrombin, as described herein. In some embodiments, the hydrogel is constructed from one or more biomolecules, for example, fibrin that supports and/or promotes the ingrowth of new blood vessels. The hydrogel coating may be constructed from one or more biomolecules that support blood vessel maturation and/or stability.

The hydrogel may include one or more angiogenic factors, for example, vascular endothelial growth factor (VEGF), fibroblast growth factor (FGF), platelet-derived growth factor (PDGF), angiopoeitins (Ang-1, Ang-2), transforming growth factor (TGF-β), and the like, as described herein. In some embodiments, the biocompatible hydrogel is seeded with a plurality of cells, as described elsewhere herein. For example, in some embodiments the hydrogel is seeded with pancreatic islet cells.

In some embodiments of the invention, cells may be injected into the wall of the vascular graft as a means of trapping the cells or islets therein. In certain applications, cells or islets may be entrapped within particles, microparticles, or sheets of extracellular matrix material that is bound to the outside of the vascular graft. Alternatively, cells or islets may be encapsulated in microparticles or sheets of synthetic material that is suitable for implantation, and that is affixed to the outside of the vascular graft.

The decellularized vascular graft 120 may be placed in a suitable container such as, for example, a syringe containing a solution of one or more biomolecules (e.g., fibrin, etc) and/or one or more cells and/or islets. The decellularized vascular graft 120 may be incubated in a solution of biomolecules and/or cells and/or islets for a period of time sufficient for a hydrogel to form. For example, the decellularized graft 120 may be incubated for up to 5 minutes, 5 minutes to 30 minutes, 30 minutes to 60 minutes, 1 hour to 3 hours, 3 hours to 6 hours, 6 hours to 12 hours, 12 hours to 24 hours, and the like.

In various embodiments of step S903, BVP 100 is implanted in a subject in need thereof. In some embodiments, BVP 100 can be directly interconnected with a subject's bloodstream as understood by those skilled in the art. In some embodiments, BVP 100 is connected to one or more blood vessels of the pancreatic circulation. In some embodiments, the BVP is connect to one or more blood vessels of the hepatic circulation. In some embodiments, the BVP is connected as an arteriovenous fistula between an artery and vein. In some embodiments the arteriovenous fistula is located on an extremity, for example on an arm or upper extremity, or a front limb. In some embodiments, the fistula is located on a leg or lower extremity, or a hind limb. In some embodiments, the BVP is implanted in any suitable location within a subject, as understood by those skilled in the art, such as an arterial bypass graft, a venous bypass graft, an arterial interposition graft, a venous interposition graft, a sub-cutaneous implant, a mesenteric implant, a portal vein implant, or other implantation location. In some embodiments, the subject is mammalian, for example, human.

In some embodiments, when the subject is treated using the composition, systems and/or methods of the present invention, the disease or disorder, for example type I diabetes, is improved. In some embodiments, when the subject is treated using the composition, systems and/or methods of the present invention, the symptoms of the disease or disorder are alleviated. In some embodiments, when the subject is treated using the compositions, systems and/or methods of the present invention, the subject is provided with one or more biomolecules, for example insulin.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Design of a Bioartificial Vascular Pancreas to Treat Type I Diabetes

As an innovative and potentially impactful approach to solving some of the problems with islet transplantation, the delivery of pancreatic islets on the outside of a decellularized vessel was investigated. After seeding the islets on the outer surface of the decellularized vessel, the tissue is implanted as a vascular graft, with arterial blood flow coursing through the lumen of the decellularized vessel, and islets embedded on the outer surface of the vessel. In the case of arterial graft implantation, fully oxygenated blood will flow directly through the decellularized vessel and allow for diffusion of oxygen and nutrients to the islets that are seeded on the outer vessel surface. The islets are then able to respond to blood sugar levels and secrete insulin into the host circulation. A visual representation of the Bioartificial Vascular Pancreas (BVP) technology is shown in FIGS. 1A-1G. The over-arching goal of this invention and technology is to help patients combat type 1 diabetes.

Pancreatic Islet Isolation

In order to test the BVP, pancreatic islets were first harvested in a robust and repeatable manner. Islet harvests were performed in both rats and pigs in to use in the BVP test trials.

Rat Islet Isolation: The protocol for rat islet isolation was based on a protocol by Carter et al with several modifications found to improve yield (Carter, et al., Biological Procedures Online 2009; 11:3-31). Pancreatic rat islet harvests were performed on female Sprague Dawley rats aged 2-4 months weighing 200-300 g. To sacrifice the animals, Euthasol was injected intraperitonially at 175 mg/mL and at 0.1 mg/100 g rat. Hank's Balanced Salt Solution (HBSS) supplemented with HEPES buffer solution and Penicillin/streptomycin antibiotic (P/S) was utilized as a buffering/washing solution. After incision and opening of the abdominal cavity, the common bile duct was located and cannulated with 10 mL of collagenase P in HBSS at 1.5 mg/mL using a 25-gauge needle. The pancreas was then excised. The extracted pancreas was placed in a glass vial containing an additional 10 mL of collagenase P. The glass vial was then placed in a water bath and continuously agitated for 10-14 minutes in order to allow the collagenase to digest the pancreas. Once no large tissue chunks remained, the solution was washed 3× using Hanks Balanced Salt Solution (HBSS) buffer. For each wash, the cells were allowed to settle for 4 minutes and the supernatant was aspirated away. Following three washes, two additional washes were performed using 1000 μm mesh as filters to remove larger tissue particulate. Finally, for the last wash, the cells were placed into a 70 μm cell strainer and washed with HBSS. This allowed exocrine clusters and cells to be filtered through while keeping islets on the mesh. The mesh was then rinsed onto a non-treated petri dish using Roswell Park Memorial Institute (RPMI) media. 10 drops of dithizone (0.025 g dithizone; 5 mL DMSO; 20 mL PBS) were added to the petri dish to stain islets pink. Islets were then handpicked and cultured in RPMI (RPMI, 10% fetal bovine serum, 1% P/S) for use. Rat islets and rat islets stained using fluorescein diacetate/propidium iodide (FDA/PI), which stains live cells green and dead cells red, are shown in FIG. 2B.

Porcine Isolation: Porcine islets were also isolated. 100 mL of 1.5 mg/mL collagenase P was injected through the common bile duct of the porcine pancreas after organ extraction. The pancreas was then placed in a glass bottle and digested for 20 minutes. During the last minute, the bottle was agitated for a full minute. The islets were then washed and isolated using a process identical to that described for rat pancreases. Porcine islets stained using FDA/PI are shown in FIG. 3. These data show that it is feasible to harvest viable islets from several species, and such techniques can be extended to isolate islets from human pancreases. For clinical implementation of the BVP, it is anticipated that human islets would be transplanted into the recipient, not animal-derived islets. Human islets may be isolated from human pancreases using any one of a number of methods that are known in the art. The animal-derived islets described here are used for purposes of pre-clinical proof of principle studies, described below.

Decellularizing Vessels

Native arteries were isolated from rat and human tissues, and then subjected to decellularization. Other potential decellularized arterial grafts that could be utilized for the BVP invention include decellularized adult human vein or artery, and also decellularized engineered arteries/blood vessels. For purposes of the proof-of-principle studies here, human umbilical arteries and native rat aortas were utilized, because their diameter (~1 mm) is suitable for implantation into the abdominal aorta of a rat.

A protocol from Gui, et. al., was used to decellularize human umbilical arteries and rat thoracic aortas (Gui, et al., Tissue Eng Part A 2009; 15: 2665-76). To isolate human umbilical arteries, human umbilical cords were obtained.

The arteries were isolated by cutting through the umbilical cord with tweezers. Rat thoracic arteries were isolated by opening the chest wall of sacrificed rats and cutting the aortas out. The decellularization process was initiated by incubating isolated vessels in CHAPS detergent solution (8 mM CHAPS; 1 M NaCl; 25 mM EDTA) overnight. The vessels were then washed and incubated in SDS detergent solution (1.8 mM SDS; 1 M NaCl; 25 mM EDTA) overnight at 37° C. Fifteen washes with PBS were then performed in order to clear out any CHAPS or SDS from the vessels. The decellularized vessels were then kept for up to a year in at 4° C. in sterile Phosphate buffered saline with 1% Penicillin/streptomycin antibiotic solution.

Fibrin Coating

After preparation of the decellularized arteries, a hydrogel coating was developed that would be suitable for attaching the islets to the outer surface of the decellularized graft. In choosing a suitable hydrogel, it is important that it be biocompatible, mechanically stable, and, preferably, angiogenic. While any one of a number of hydrogels might be suitable for this purpose of producing the BVP, in these proof of concept studies, fibrin was utilized. This hydrogel was chosen because of its high biocompatibility, excellent support for angiogenesis, and also for its ability of the stiffness of the hydrogel to be tuned, depending upon the relative ratios of fibrinogen and thrombin that are used to create the gel. By tuning the stiffness of the fibrin gel, the mechanical properties of the islet-containing coating surrounding the outside of the acellular artery can be varied, which could allow for optimization of gel stability to withstand the physical rigors of surgical implantation.

Fibrin hydrogel is created using mixtures of fibrinogen and thrombin. The thrombin acts to cleave the fibrinogen molecules and to form crosslinked networks of fibrin. To optimize the fibrin coating, the fibrin composition was tested using varying concentrations of fibrinogen in multiple ratios with thrombin. 5 mg/mL fibrinogen in a 5:1 ratio with thrombin; 10 mg/mL fibrinogen in a 5:1 ratio with thrombin and 10 mg/mL fibrinogen in a 10:1 ratio with thrombin were coated onto decellularized human umbilical arteries using a molding technique. Briefly, the decellularized arteries were threaded through a 10 cm 14-gauge metal syringe. A 1 mL plastic syringe was then coated with 5% pluronic which is hydrophobic in order to prevent fibrin from sticking to the inner lumen of the syringe. Fibrin was loaded into the 1 mL syringe, and the metal syringe with the umbilical artery were placed inside the syringe. The fibrin was allowed to polymerize around the vessel. 1.5 mM $Ca^{2+}$ was also added to increase fibrin polymerization. After 30 minutes of incubation at 37° C., the metal syringe was extracted from the plastic syringe and this maneuver resulted in a decellularized vessel coated in fibrin. This process is shown in FIGS. 4A-4D. An exemplary decellularized vessel coated in fibrin and released from the metal syringe support structure is shown in the fourth panel of FIG. 4D. Qualitatively, 10 mg/mL fibrinogen in a 10:1 ratio with thrombin resulted in the best coating.

MIN6 Cell Culture

As described herein, techniques were developed to isolate purified pancreatic islets from rat and pig tissues. It is these islets that will be embedded in the fibrin coating surrounding the acellular artery, to create the BVP. However, islets are cumbersome to work with and can be expensive to isolate and maintain. Therefore, to speed the initial proof-of-concept studies, an immortalized cell line was utilized that produces insulin at high efficiency.

Figure 5:
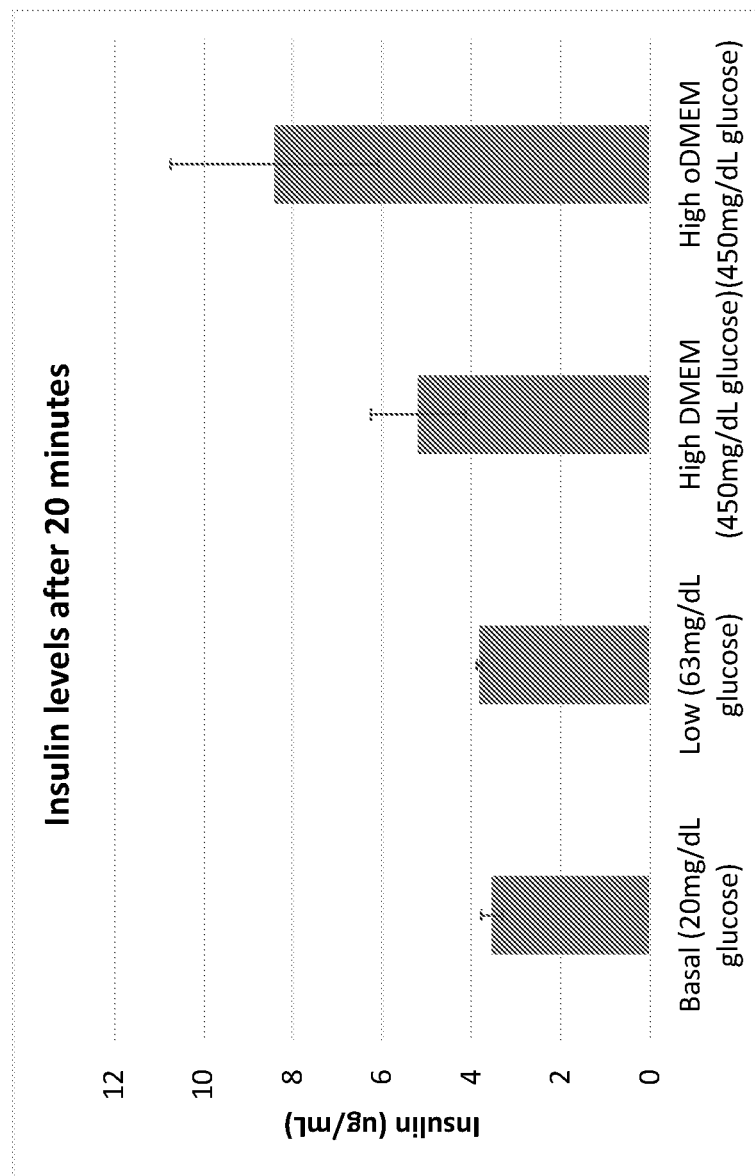
FIG. 5 depicts results from a MIN6 glucose-stimulated insulin secretion test. Insulin levels were detected 20 minutes after incubating MIN6 cells with varying concentrations of glucose. The cells exhibited higher insulin secretion when exposed to higher levels of glucose which is similar to the behavior of native pancreatic islets.

Mouse insulinoma (MIN6) cells were utilized as a model cell type for initial tests of the BVP system. Glucose stimulated insulin secretion (GSIS) experiments were performed to demonstrate that MIN6 cells can produce insulin in response to glucose, at levels that are similar to native islets. To perform this experiment, 50,000 MIN6 cells were cultured in 24 well plates and the cells were allowed to settle overnight. Culture medium was removed and the wells were washed with PBS. Basal medium with low glucose (20 mg/dL glucose) was incubated with the cells for 2 hours. Glucose at varying concentrations and optimized DMEM were then applied onto the cells and incubated for 20 minutes. Insulin was detected using an insulin (enzyme-linked immunosorbent assay) ELISA assay from Mercodia, Inc. Insulin levels after 20 minutes are shown in FIG. 5 and demonstrate a successful GSIS response, with especially high insulin secretion observed using high glucose optimized DMEM (450 mg/dL glucose).

Figure 6:
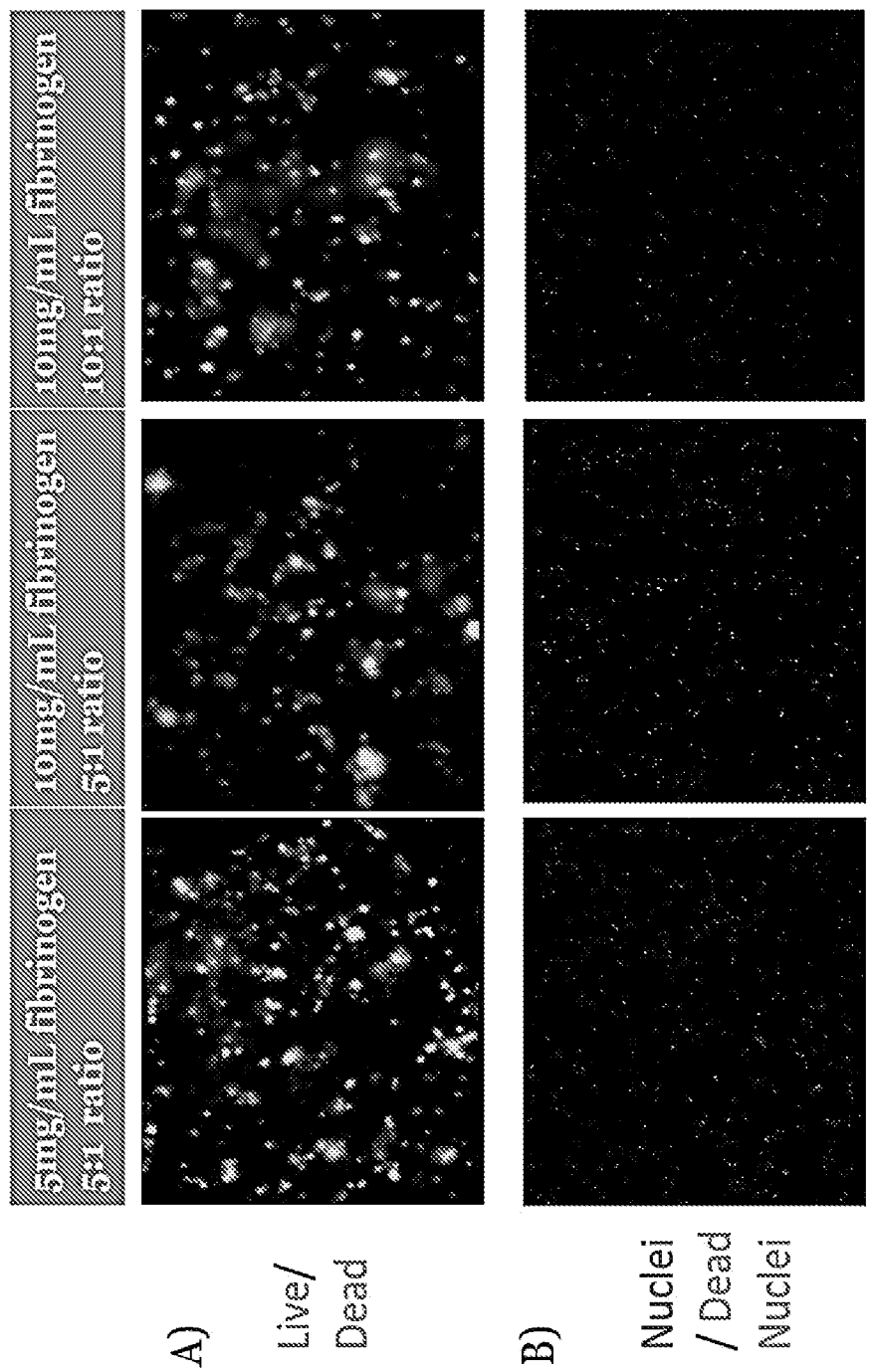
FIG. 6 illustrates exemplary results from MIN6 survival studies in fibrin gels. Two assays were performed in order to determine whether MIN6 cells could survive for extended periods of time inside various fibrin compositions.

MIN6 cells were also tested for survival in fibrin gels. 50,000 MIN6 cells were seeded into 300 μL of fibrin gel at varying fibrinogen concentrations and fibrinogen-to-thrombin ratios. The cell-laden fibrin constructs were kept in 500 μl of optimized DMEM media for 3 days. Survival was demonstrated using fluorescein diacetate/propidium iodide (FDA/PI) which stains live cells green and dead cells red. FIG. 6, row A shows that a majority of cells are green and survive, regardless of the fibrin composition. Terminal deoxynucleotidyl transferase dUTP nick end labeling (TUNEL) staining was used as a second validation for survival. TUNEL stains dead nuclei green and DAPI was used to stain cell nuclei blue. FIG. 6, row B shows that the majority of nuclei are not green, and thus the cells survived inside of the gels.

Islet Functionality in Fibrin

Figures 7A, 7B:
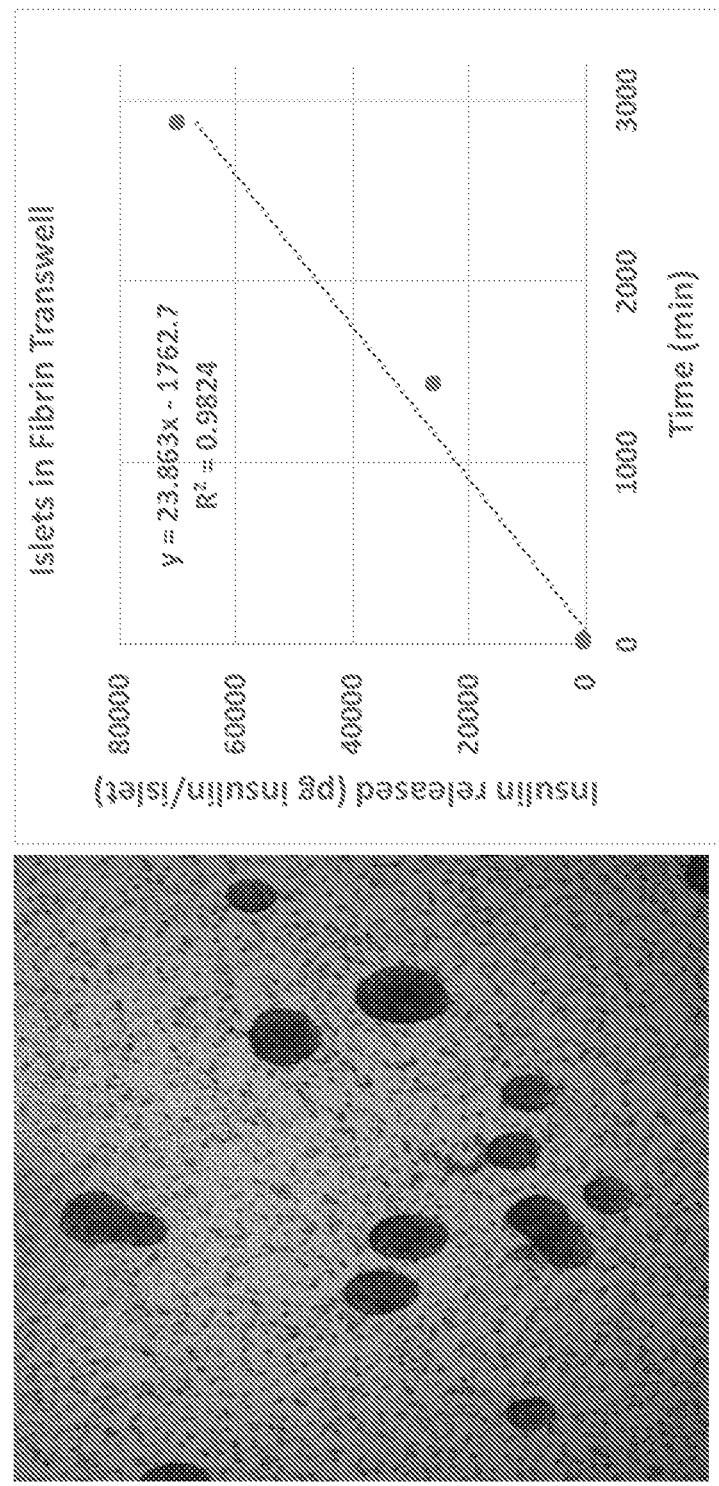
FIGS. 7A and 7B depict experimental data from insulin release experiments with cultured islets in fibrin.

After establishing that MIN6 cells could survive in fibrin, islets were then shown to also survive and function in fibrin. Islet culture in fibrin was evaluated using a transwell setup. The transwell setup provides an ideal condition to surround islet seeded fibrin gels with medium. Thirty rat islets were encapsulated inside 10 mg/mL fibrin and cultured inside transwell inserts for 2 days. A light microscopy photograph for these islets is shown in FIG. 7A. During these two days of culture, insulin levels were determined using insulin ELISAs in order to detect insulin release from the islets. This insulin release can be found in FIG. 7B, and the slope demonstrates that the islets release insulin at 23 pg/islet/minute, which is close to the 20 pg/islet/minute value found in literature (Buchwald, Theoretical Biology and Medical Modelling 2011; 8: 20). This shows that the islets are able to successfully function inside of a fibrin gel, supporting the use of a fibrin coating for creating the BVP constructs.

Finite Element Analysis

Figure 15A:
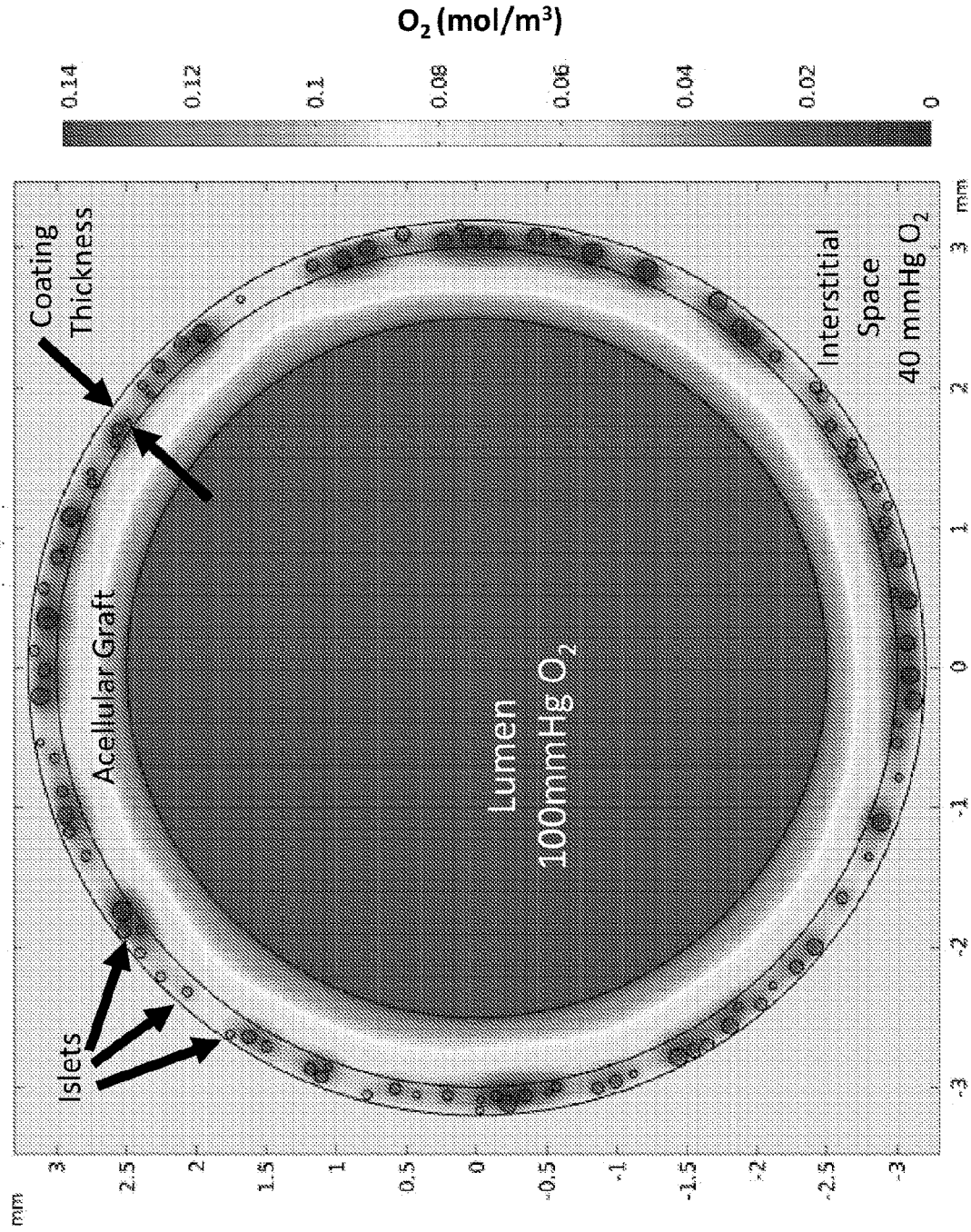
FIG. 15A depicts results from finite element analysis performed in COMSOL Multiphysics® software. Modeling shown simulates oxygen diffusion in the BVP construct. The simulated islets, acellular graft, and hydrogel coating are assigned diffusion coefficient values. Oxygen originates from the lumen and interstitial space and must diffuse through the acellular graft and hydrogel coating to reach the pancreatic islets which consume oxygen.
Figure 15B:
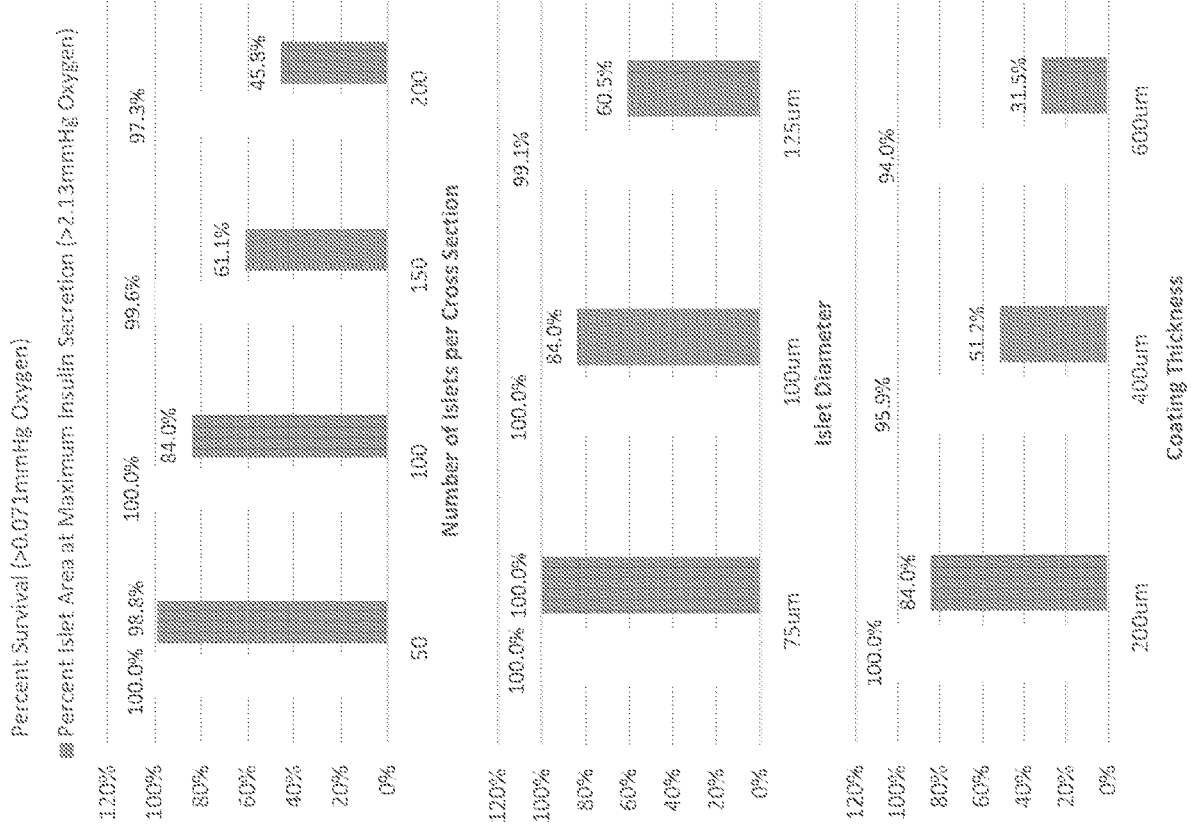
FIG. 15B depicts results from finite element analysis showing islet percent area that is above 0.071 mmHg oxygen which allows for islet survival, and above 2.13 mmHg oxygen which allows for full uninhibited secretion of insulin.

In order to determine optimal BVP preparation conditions in order to allow for maximum islet survival, finite element analysis was performed using COMSOL Multiphysics® cross-platform finite element analysis simulation software. Modeling, shown in FIG. 15A, simulates oxygen diffusion in the BVP construct. The simulated islets, acellular graft, and hydrogel coating are assigned diffusion coefficient values. Oxygen originates from the lumen and interstitial space and must diffuse through the acellular graft and hydrogel coating to reach the pancreatic islets which consume oxygen. The simulation was used to evaluate percentage islet survival and percentage islet area at maximum insulin secretion with varying numbers of islets per cross section, varying islet diameter, and varying hydrogel coating thickness. Simulation results, shown in FIG. 15B are presented for islet percent survival for oxygen levels that are above 0.071 mmHg oxygen which allows for islet survival, and for islet area at maximum insulin section for oxygen above 2.13 mmHg oxygen, which allows for full uninhibited secretion of insulin. Parameters such as number of islets per cross section, islet diameter, and hydrogel coating thickness were varied to determine their effects on islet survival and functionality.

Bioreactor Setup

Figure 8:
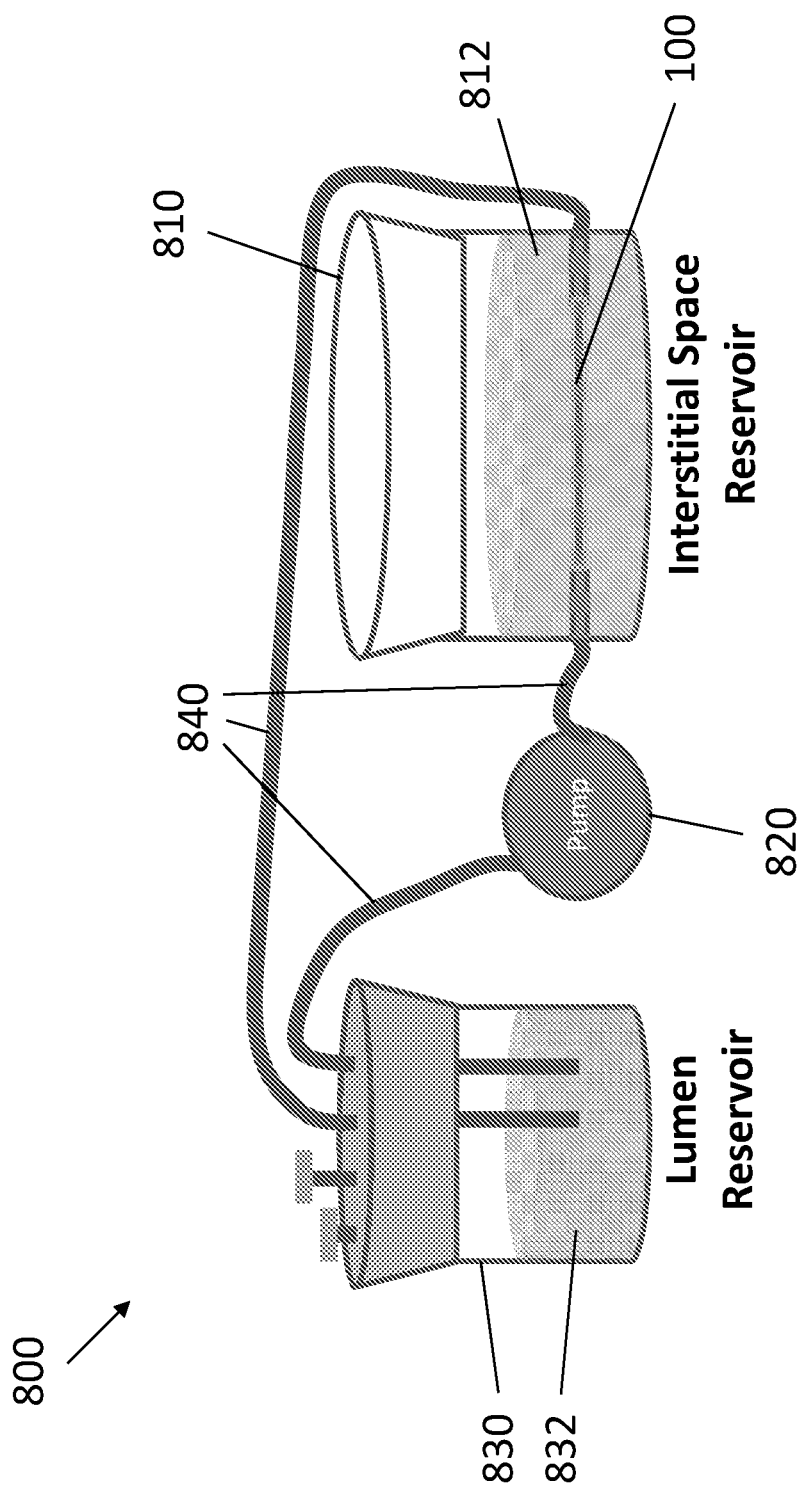
FIG. 8 illustrates an exemplary BVP bioreactor design. A bioreactor setup is depicted that was initially used to evaluate the performance of the BVP concept in vitro. The bioreactor is designed to simulate the in vivo environment into which the BVP is implanted. The lumen reservoir contains high oxygen and glucose levels and represents luminal blood flow once the BVP is implanted. A pump operates to flow media from the lumen reservoir through the BVP and back into the lumen reservoir. The interstitial space reservoir contains low oxygen and glucose levels in order to simulate the tissue conditions that would be around the BVP once it is implanted.

In order to prove that the BVP invention is a suitable environment to maintain survival of cells encapsulated within a hydrogel on the outer surface, initial tests using the BVP setup were performed in bioreactors. The bioreactor was designed and constructed to replicate the in vivo environment that would be experienced by an implanted BVP. An implanted BVP would experience high glucose and oxygen from the lumen, and lower oxygen and glucose levels from the surrounding interstitial space. To replicate this in vitro, the bioreactor was segmented into two reservoirs. A lumen reservoir containing optimized DMEM with 450 mg/dL glucose and attached air filters. Outside of the BVP, there was an interstitial reservoir, containing glucose-free DMEM with <20 mg/dL glucose with no air filters. A BVP construct can be sutured into the bioreactor, and media from the lumen reservoir can be pumped through the lumen of the BVP. The bioreactor design is shown in FIG. 8.

Figures 9A, 9B, 9C:
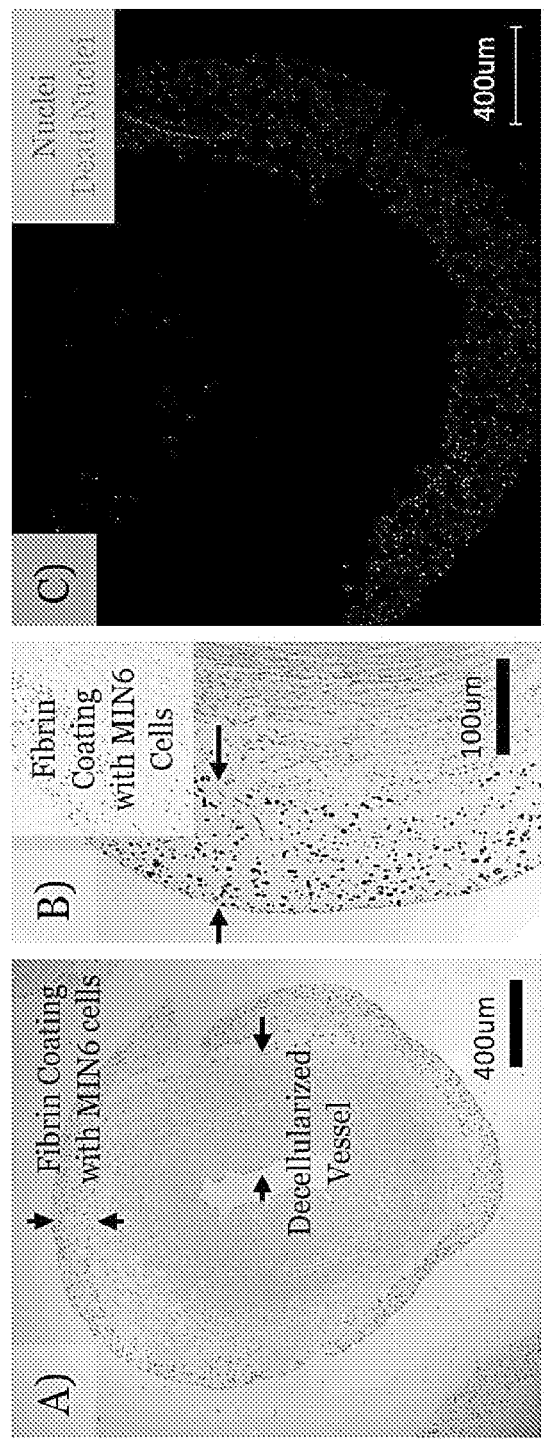
FIGS. 9A-9C provide experimental results from MIN6 BVP bioreactor studies. Decellularized vessels coated with fibrin and MIN6 cells were cultured inside of the bioreactor shown in FIG. 8, as described herein, for 3 days. Following this period, the vessel was taken out, preserved with fixative and mounted onto slides for analysis.

Preliminary studies utilized MIN6 cells that were coated around decellularized umbilical arteries using 10 mg/mL fibrin as previously described. The MIN6 BVPs were cultured inside the bioreactor at 37° C. for 3 days. The results after 3 days in bioreactor culture are shown in FIGS. 9A-9C. Hematoxylin and eosin (H&E) staining was used to identify the cells. Hematoxylin stains DNA and nuclei dark blue in order to identify cells, while eosin stains proteins pink. Cells remained coated around the surface of the decellularized vessel, and TUNEL staining demonstrated cell survival. These data suggest that the BVP provide enough oxygen and nutrients to cells that are seeded on the outer surface of a decellularized vessel.

Static Insulin Production

Figure 16A:
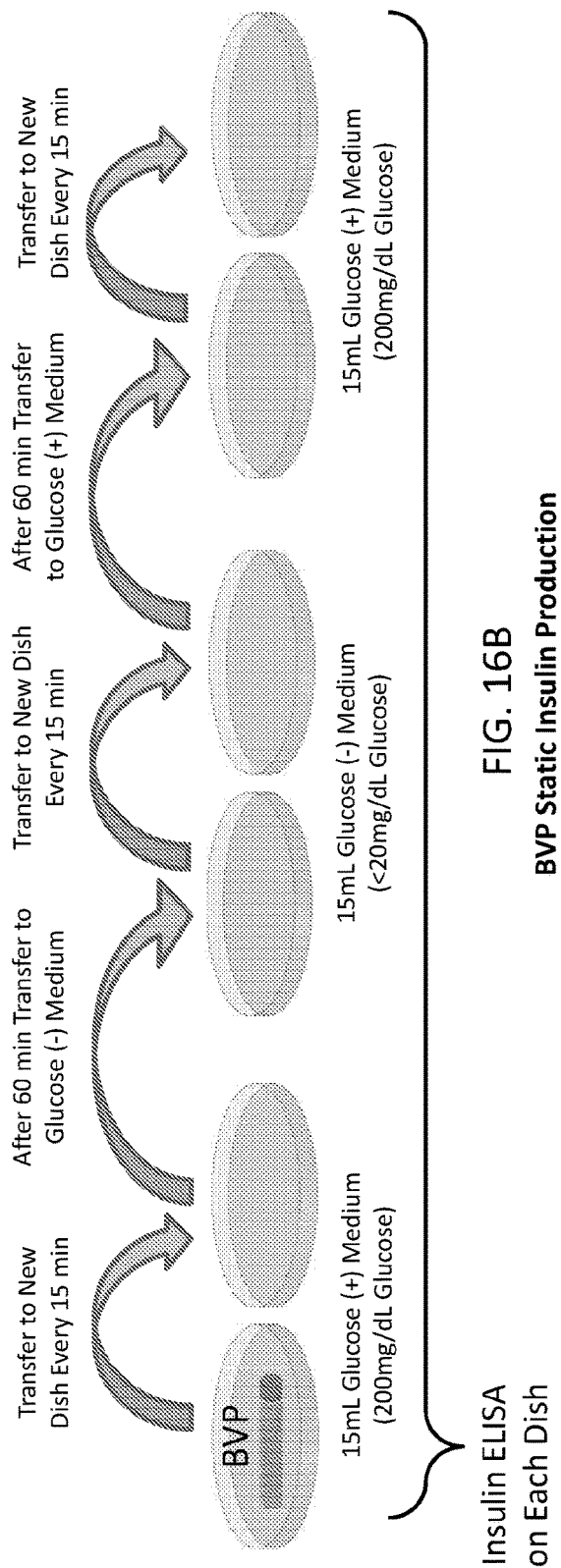
FIG. 16A depicts an exemplary setup for a static insulin production experiment. The BVP is placed into a dish of either glucose (+) media or glucose (−) media. Pancreatic islets will secrete insulin when exposed to the high glucose levels of the glucose (+) media and will halt insulin production when exposed to low glucose levels in the glucose (−) media.
Figure 16B:
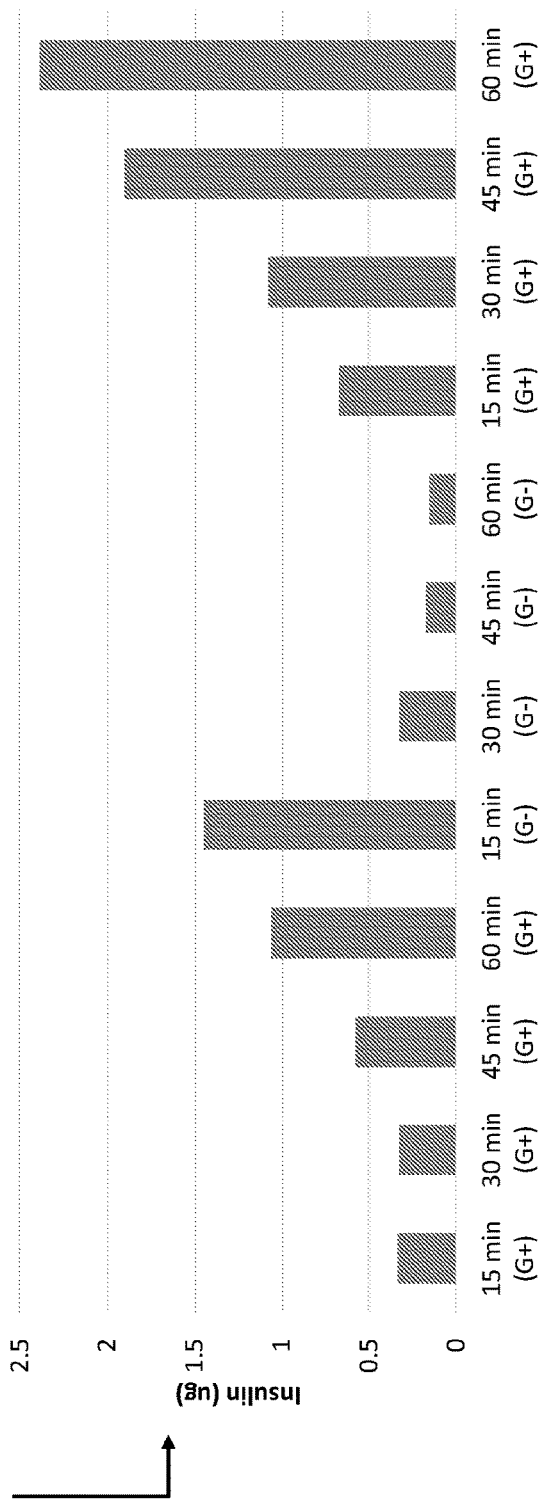
FIG. 16B depicts insulin ELISA results demonstrating that the BVP is capable of responding to glucose by secreting insulin.

In order to evaluate insulin production of pancreatic islets within a BVP, the BVP is placed into a dish of either glucose-containing (glucose (+)) media or glucose-free (glucose (−)) media, according to the experimental parameters shown in FIG. 16A. Briefly, the BVP is placed in a dish containing glucose (+) media, and transferred to a new dish with fresh media every 15 minutes for a 60 minute period. The BVP is then transferred to a dish containing glucose (−) media. The BVP is again transferred to a new dish containing fresh glucose (−) media every 15 minutes for 60 minutes. The BVP is then transferred back to a dish containing glucose (+) media. The BVP is again transferred to a new dish containing fresh glucose (+) media every 15 minutes for 60 minutes. ELISA analysis for insulin was performed on media collected from each dish over the course of the experiment. Pancreatic islets secrete insulin when exposed to the high glucose levels of the glucose (+) media. Pancreatic islets halt insulin production when exposed to low glucose levels in the glucose (−) media. Results, shown in FIG. 16B, demonstrate insulin ELISA results indicating that the BVP is capable of responding to glucose with insulin secretion.

In Vivo Implantation

After the initial success of the BVP in vitro, the construct was tested in vivo. Immunodeficient Rowett Nude (RNU) rats were utilized for the in vivo studies. The rats were purchased from Charles River at 5 months of age. To generate the BVP constructs, decellularized human umbilical arteries were seeded on their outer surfaces with ~200 porcine islets inside 10 mg/mL fibrin as previously described. The BVP constructs were implanted in the nude rats using an aortic interposition graft protocol. The freshly implanted BVP can be seen in FIG. 10A.

Figures 10A, 10B:
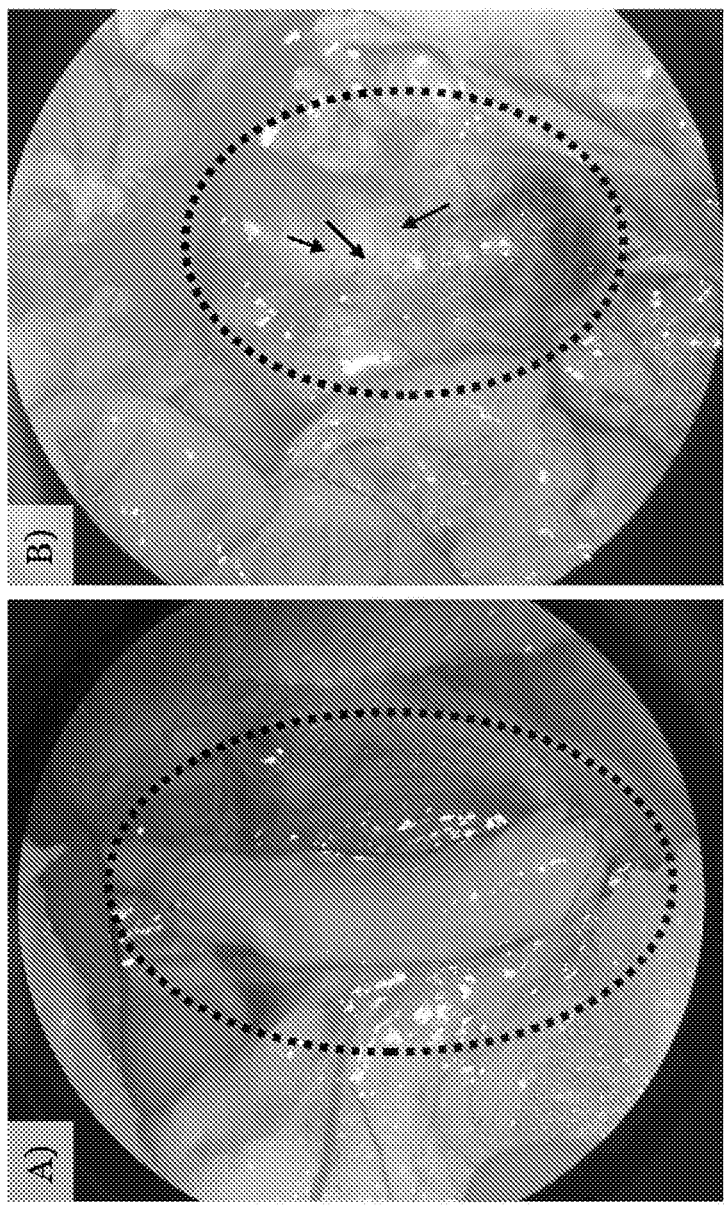
FIGS. 10A and 10B illustrate an exemplary BVP in vivo. BVP constructs were generated by coating porcine islets around a decellularized human umbilical artery using fibrin. These constructs were then implanted into nude rats as arterial interposition grafts.

Rats recovered quickly from the surgery and were fully active within 24 hours. Two weeks after implantation, the BVP constructs were explanted. The BVP construct after 2 weeks in vivo is shown in FIG. 10B. Small microvessels had grown over the BVP construct which shows that the implant had promoted angiogenesis into the fibrin coating. This angiogenesis can provide further nutrients for the islets coated on the BVP surface. This fundamentally makes the BVP technology different than other islet technologies that focus on walling off islets from their surroundings through the use of semipermeable membranes. Rather, the BVP provides nutrients via diffusion from the lumen of the vascular graft, and subsequently provides additional nutrients to islets via the formation of capillaries that come into close proximity with the islets on the outer surface of the vascular graft. The BVP grafts remained patent for the entire experiment.

Figure 11B:
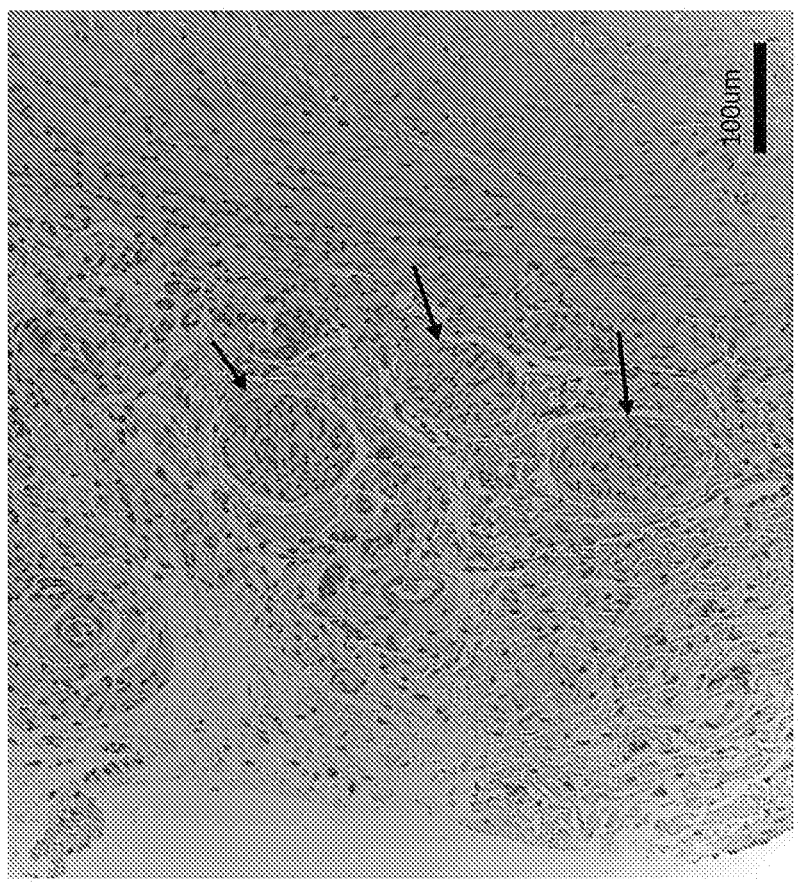
FIGS. 11A and 11B illustrate exemplary H&E staining of explanted BVP after 2 weeks in vivo. Explanted BVP constructs were stained using H&E.
Figure 11A:
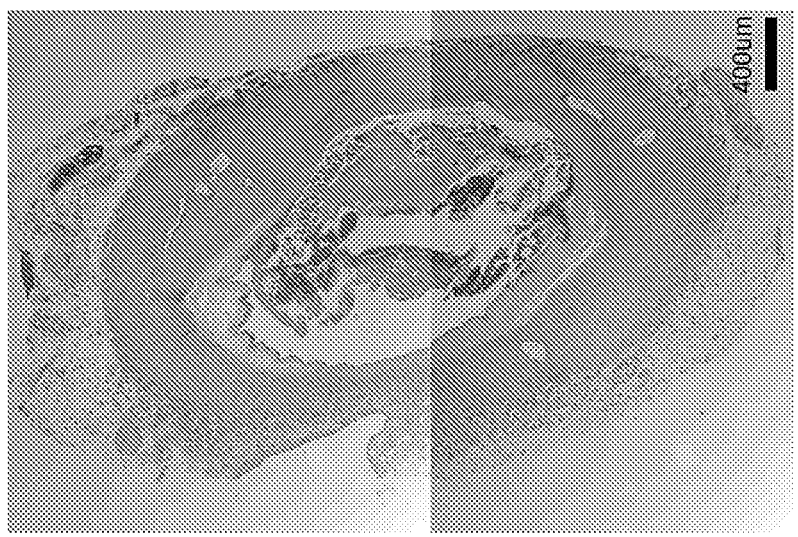
Figure 12:
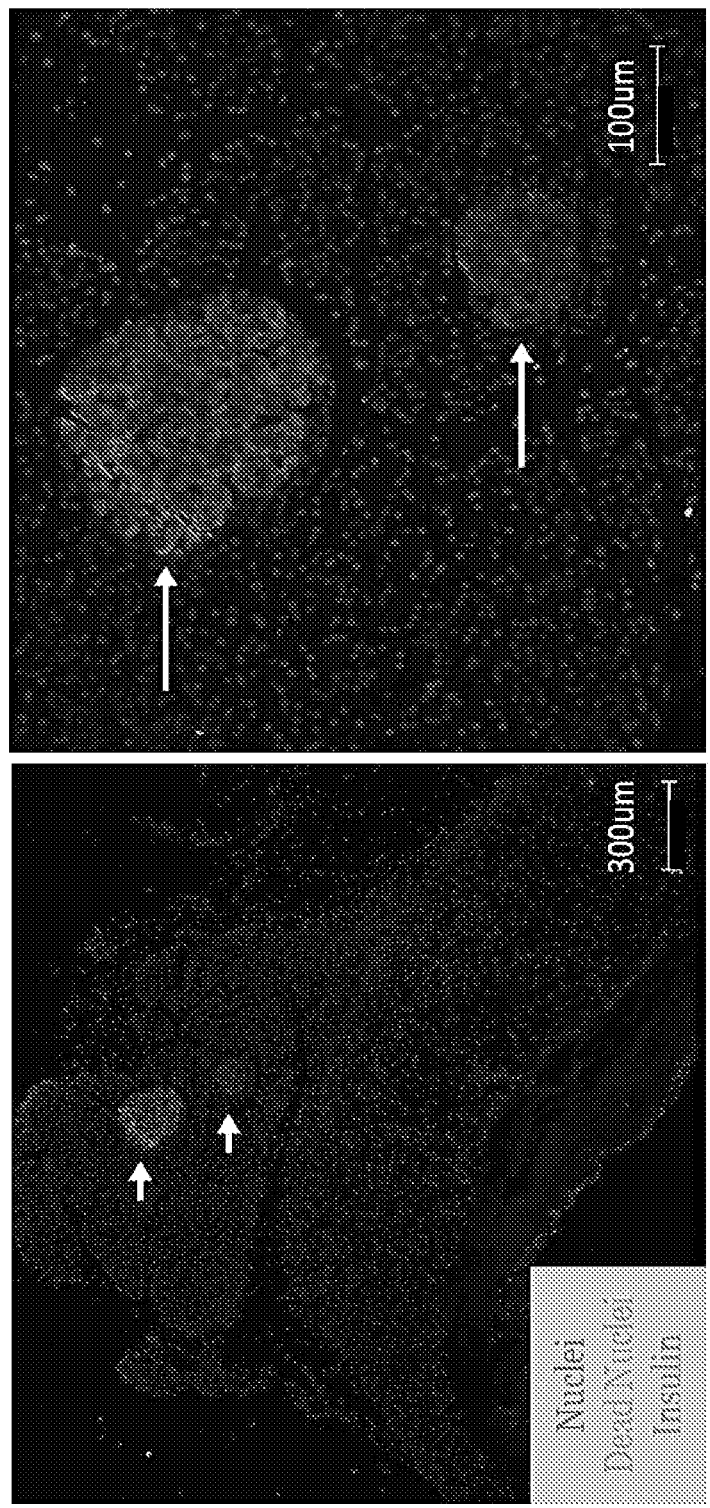
FIG. 12 depicts exemplary immunofluorescent imaging for evaluating cell survival after explantation of the BVP from the rat in the aortic grafting position. Immunofluorescent images are depicted with DAPI staining showing nuclei as blue (dark area), TUNEL staining showing dead cells as green (none depicted), and insulin staining showing islets as red (highlighted with arrows). The red clusters are the insulin secreting islets indicated with arrows. There is no presence of green in the islets showing that they survived implantation into the host for the full 2 week experiment.
Figure 13:
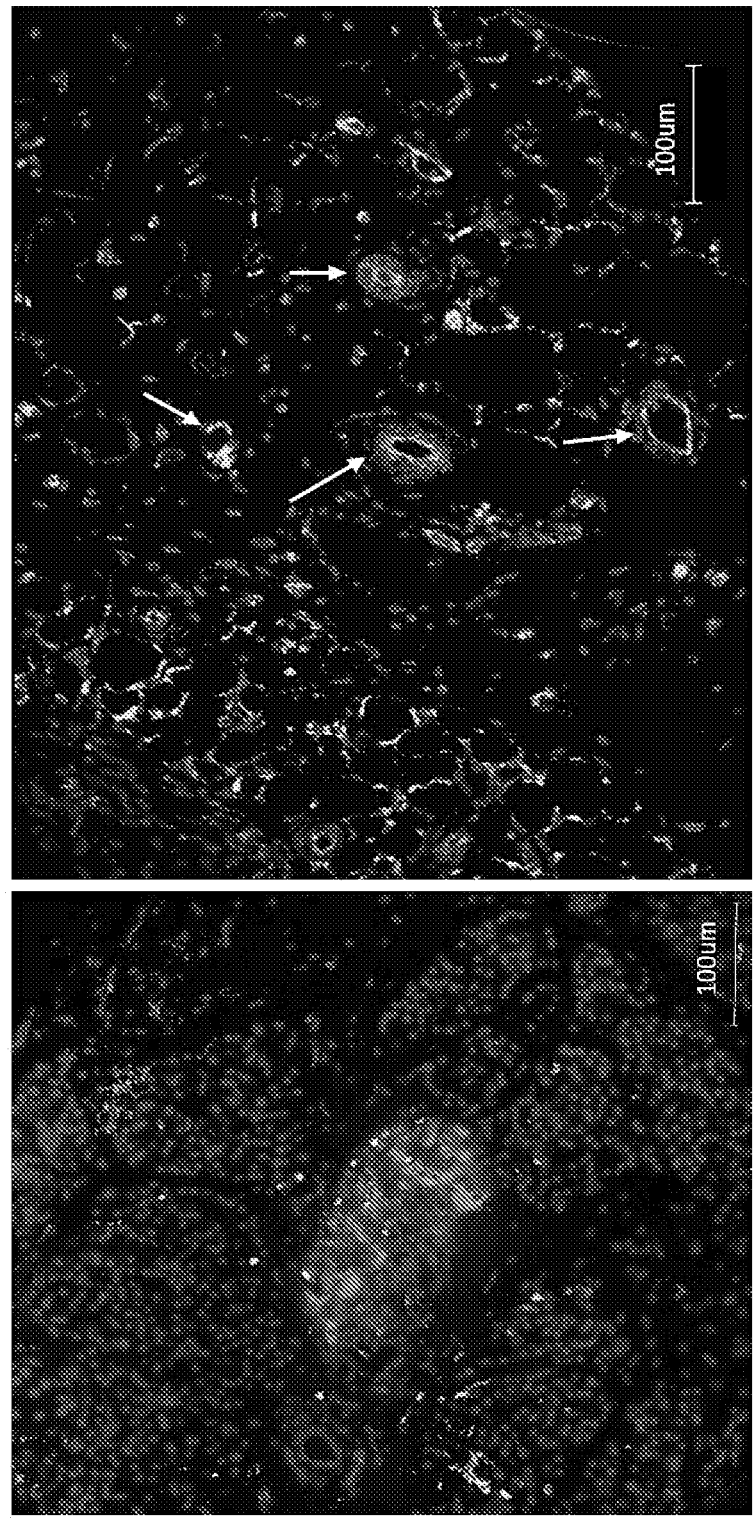
FIG. 13 illustrates immunofluorescent imaging for microvasculature growth. Immunofluorescent images are depicted with DAPI staining showing nuclei as blue, CD31 staining showing endothelial cells as green, and insulin staining showing islets as red. Islets can be found embedded in fibrin with endothelial cells nearby growing to form microvessels as highlighted by the arrows.

After two weeks, the explants were analyzed via histological sectioning and immunofluorescence staining. H&E staining for the explants is shown in FIG. 11. Islets can be seen in the H&E sections of the explanted BVP. In FIG. 12, immunofluorescence staining for DAPI/insulin was used identify islets, and TUNEL was used to determine whether the islets survived. In FIG. 13 staining for DAPI/insulin was again used to identify islets and staining for CD31 was used to identify endothelial cells which shows the presence of microvessel growth. The results of the staining demonstrate that the islets were able to survive in vivo implantation for 2 weeks, which directly proves that the islets received adequate nutrients to maintain survival for this period of time in vivo. Staining for endothelial cells using CD31 showed promising microvessel growth into the fibrin construct surrounding the decellularized vessel, showing improved nutrient delivery to the implanted islets via the formation of microvessels in close proximity to the implanted islets.

In addition to in vivo experiments using nude rats, a diabetic rat model was generated by treating nude rats with streptozotocin in order to induce diabetes. Results demonstrating the validation of this model, shown in FIGS. 17A-17B indicate prolonged hypoglycemia was induced and pancreatic islets were effectively destroyed.

Figure 18A:
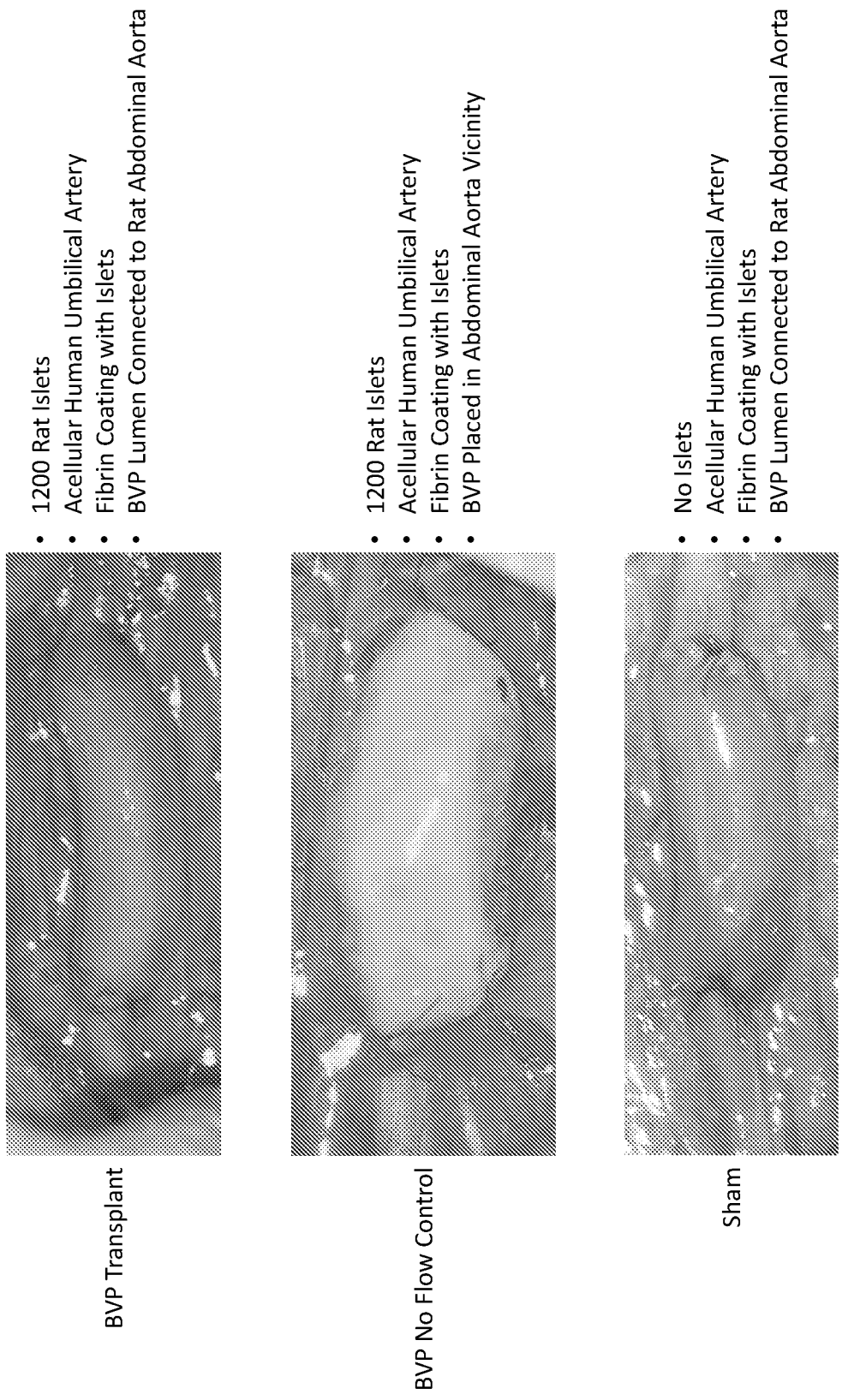
FIG. 18A depicts three types of transplants were performed on diabetic rats and blood glucose levels were monitored over time. In the BVP transplant rats, a BVP is created using 1200 rat islets, an acellular human umbilical artery, and a fibrin coating. The BVP is then sutured into the abdominal aorta of a recipient rat as an end-to-end graft. For the no-flow control, the BVP is not sutured as an end-to-end graft, but is placed in the vicinity of the abdominal aorta and held in place with 2 sutures connecting the BVP to the surrounding tissue. For the sham control, a BVP is created only with fibrin and an acellular human umbilical artery, and is then sutured into the abdominal aorta of a recipient rat as an end-to-end graft. No islets are used for this control.
Figure 18B:
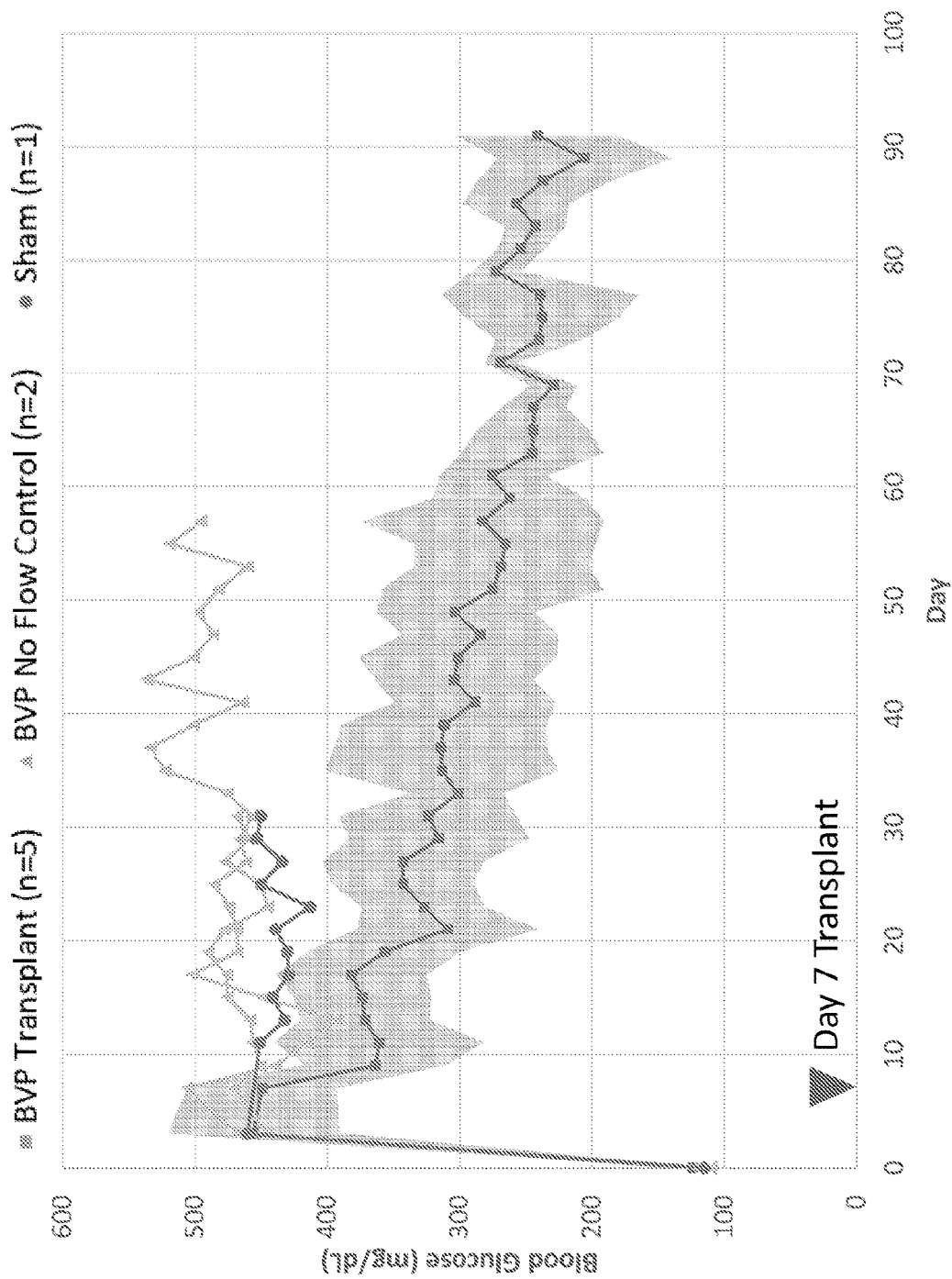
FIG. 18B depicts results from blood glucose measurements. All transplants were performed on day 7. Results indicate that transplanted BVPs are able to help lower rat blood glucose throughout the course of 90 days in comparison to the BVP no Flow Control and Sham Control.

The diabetic rats were then used to evaluate in vivo efficacy of BVP implants that were generated using 1200 rat islets seeded onto fibrin hydrogels coating acellular human umbilical artery grafts. Three surgical models were used, as shown in FIG. 18A. In the first model, the BVP was implanted such that the BVP lumen was connected to the rat abdominal aorta. The BVP was created using 1200 rat islets, an acellular human umbilical artery, and a fibrin coating. The BVP is then sutured into the abdominal aorta of a recipient rat as an end-to-end graft. In the second model, the no flow control, the BVP was implanted in the vicinity of the abdominal aorta, but the BVP is not sutured as an end-to-end graft. It is instead placed in the vicinity of the abdominal aorta and held in place with 2 sutures connecting the BVP to the surrounding tissue. This model is used to demonstrate whether flow through the lumen of the BVP is necessary for the BVP to function. In the third model, the surgical sham, the BVP was generated only with fibrin and an acellular human umbilical artery, and was then sutured into the abdominal aorta of a recipient rat as an end-to-end graft. No islets are used for this control. All transplants were performed on day 7. Results, shown in FIG. 18B indicate that transplanted BVPs are able to help lower rat blood glucose throughout the course of 90 days in comparison to the BVP no Flow Control and Sham Control.

Glucose Tolerance Test in BVP Recipients

Figure 19A:
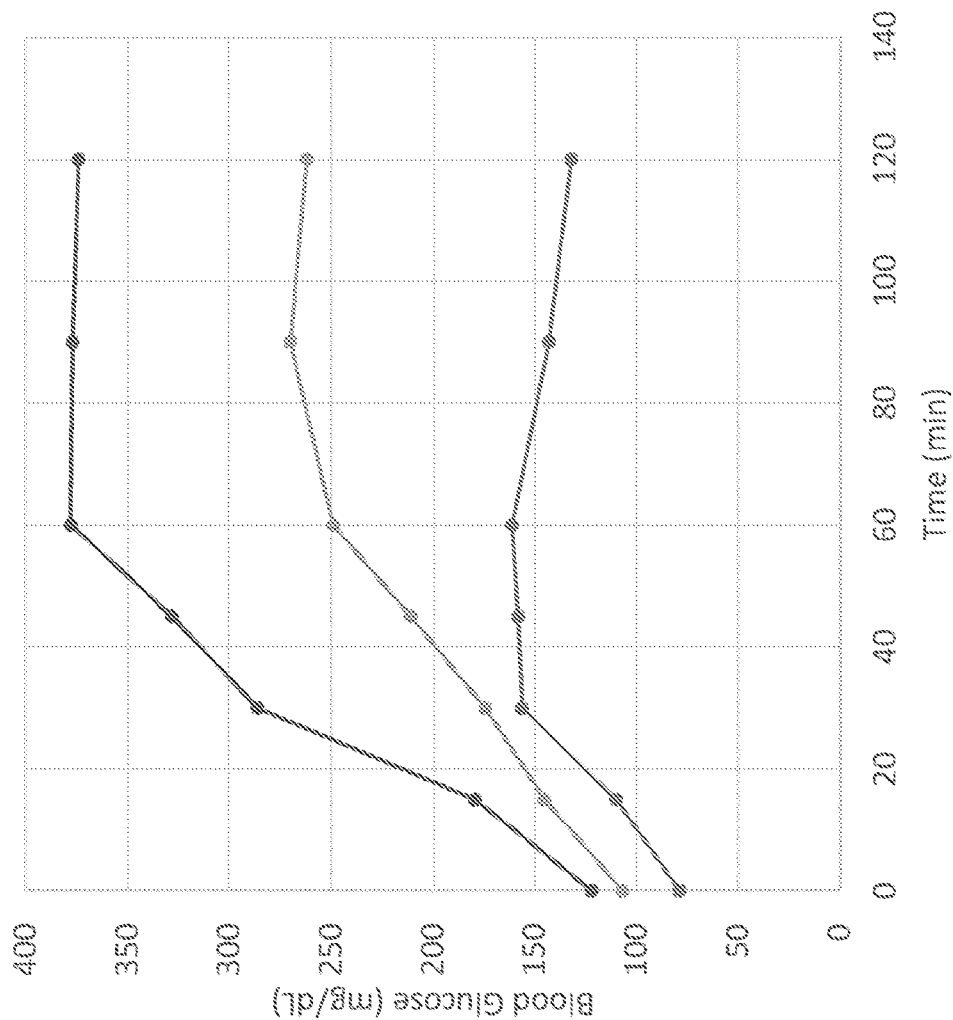
FIG. 19A depicts glucose tolerance tests that were performed on rats fasted overnight. The rats were either normal nude rats, diabetic nude rats, or diabetic nude rats that had received a BVP implantation. At time 0, the rats were intraperitonially injected with a glucose bolus at 2 g glucose/kg. Blood was then sampled using tail nicks at designated time intervals to generate the glucose tolerance test graph.
Figure 19B:
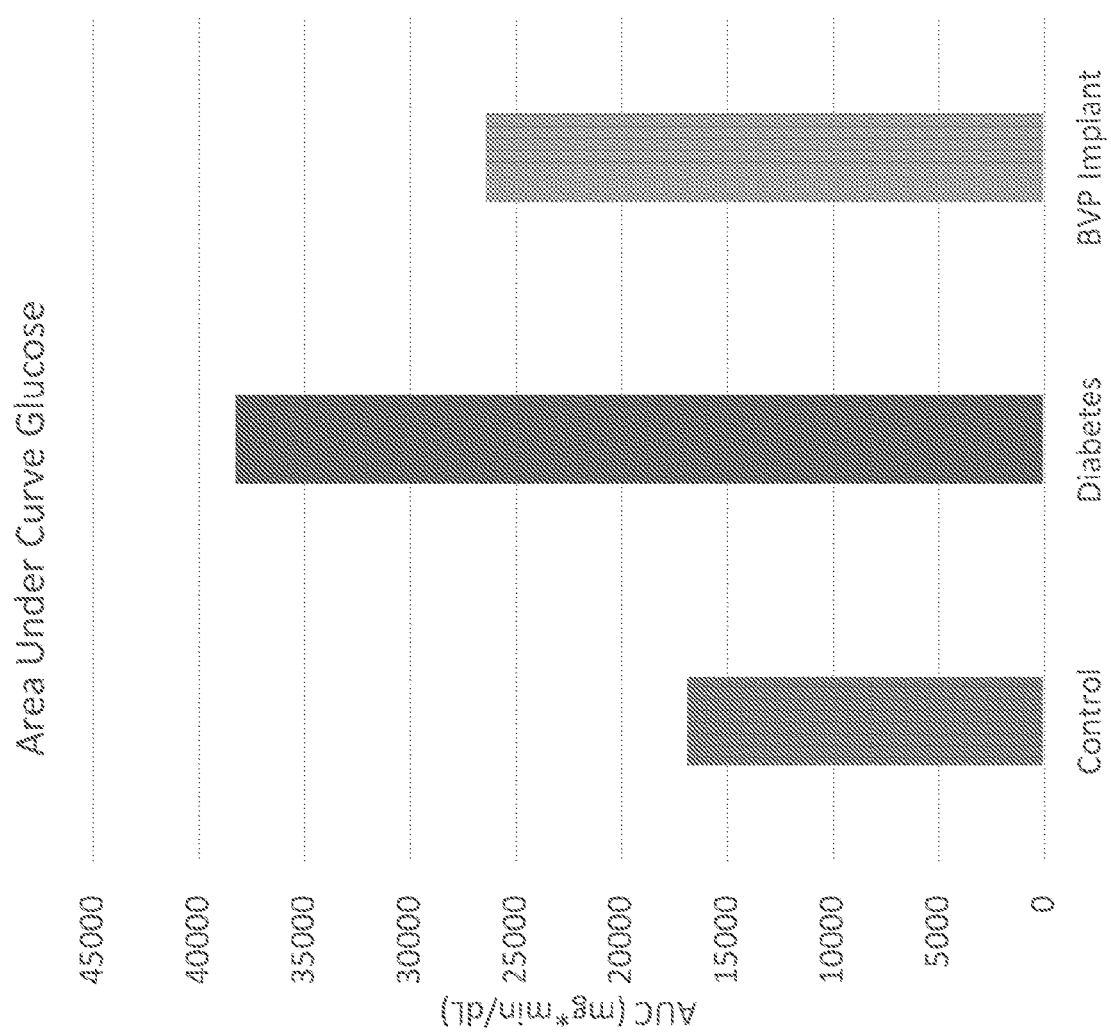
FIG. 19B depicts results using area-under-curve analysis for providing a comparison between the different groups. A small area-under-curve indicates that the rat was able to quickly restore their blood glucose level while a larger area-under-curve indicates that the blood glucose of the rat remains high for a longer period of time. The BVP implant group has a lower area-under-curve than the diabetes group but is still higher than the control rat which did not have diabetes.

Glucose tolerance tests were performed on rats fasted overnight. The rats were either normal nude rats, diabetic nude rats, or diabetic nude rats that had received a BVP implantation. At time 0, the rats were intraperitonially injected with a glucose bolus of 2 g glucose/kg rat. Blood was then sampled using tail nicks at designated time intervals to generate the glucose tolerance test graph, shown in FIG. 19A. Area-under-curve analysis was performed (shown in FIG. 19B) in order to provide a comparison between the different groups. A small area-under-curve indicates that the rat was able to quickly restore their blood glucose level while a larger area-under-curve indicates that the blood glucose of the rat remains high for a longer period of time. The BVP implant group has a lower area-under-curve than the diabetes group but is still higher than the control rat which did not have diabetes.

Insulin Production in BVPs Xenografts

Figure 20C:
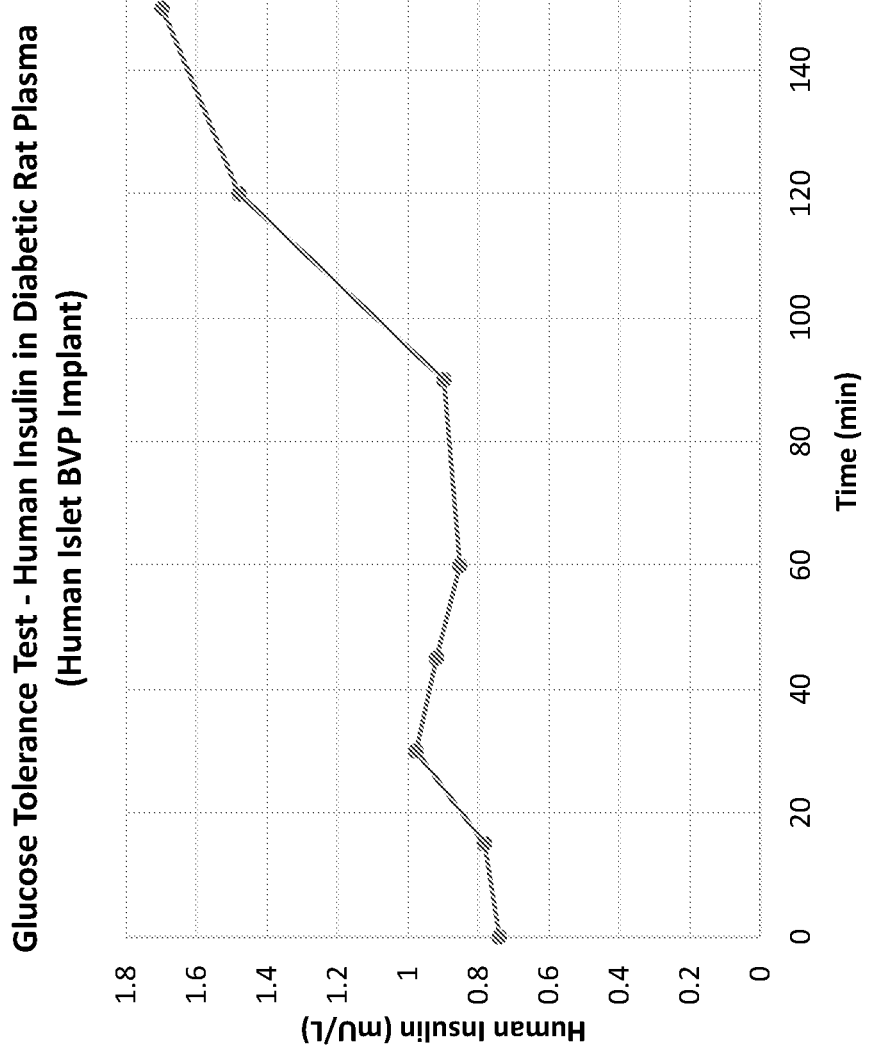
FIG. 20C depicts results from a BVP glucose tolerance test demonstrating that human insulin levels increase after glucose injection into a rat at time 0.

In addition to rat allograft BVPs generated and validated above, xenograft BVPs were generated using human pancreatic islets seeded within fibrin hydrogels coating acellular human umbilical artery vascular grafts. Xenograft BVPs were constructed using 1200 human islets, and were transplanted into diabetic rats, shown in FIG. 20A. Rat plasma was then collected at incremental time points and evaluated for human insulin. Results shown in FIG. 20B indicate that human insulin was detected in the rat plasma after transplanting the human islet BVP. In order to evaluate the efficacy of implanted BVP xenografts, glucose tolerance tests were performed on xenograft recipients. Glucose tolerance test results, shown in FIG. 20C demonstrate that human insulin levels increase after glucose injection into transplant recipient rats at time 0.

The in vitro bioreactor and preliminary in vivo implantation results demonstrate that the BVP approach to generating an ectopic pancreas has the potential to become a viable design for islet transplantation. Building on the current results, improvements are expected in islet harvest yield in order to increase the number of transplanted islets. This new technology can take advantage of an innovative transplant mechanism that provides ample nutrients and oxygen to transplanted islets, without relying on diffusion from a poorly vascularized bed such as the hepatic microcirculation or the subcutaneous space. After demonstrating the effectiveness of the BVP in animal models, BVP constructs will be created using engineered decellularized arteriovenous grafts which are 6 mm in diameter and 42 cm in length. These engineered vessels have large surface areas of 82 $cm^2$ available for islet coating, and allow for blood to flow through the lumen at approximately 1-2 liters/minute (Lawson, J. H, et al. Lancet 2016; 387(10032):2026-34.) The BVP technology offers a unique, vascular engineering solution for patients with Type I diabetes.

Although preferred embodiments of the invention have been described using specific terms, such description is for illustrative purposes only, and it is to be understood that changes and variations may be made without departing from the spirit or scope of the following claims.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition comprising:
    an acellular vascular graft having a lumen that is adapted and configured to be in direct contact with a perfusate passing through it;
    a biocompatible hydrogel encasement, wherein the biocompatible hydrogel encasement surrounds an outer surface of the acellular vascular graft; and,
    a plurality of cells, wherein the plurality of cells comprises pancreatic islet cells;
    wherein the plurality of cells are:
        a. seeded on a surface of the biocompatible_hydrogel encasement and/or
        b. seeded within the biocompatible hydrogel encasement.

2. The composition of claim 1, wherein the acellular vascular graft comprises a decellularized arterial graft.

3. The composition of claim 1, wherein the acellular vascular graft comprises a decellularized venous graft.

4. The composition of claim 1, wherein the acellular vascular graft comprises a decellularized engineered vascular graft.

5. The composition of claim 1, wherein the biocompatible hydrogel encasement comprises fibrin, fibrinogen, thrombin, collagen, elastin, gelatin, chitosans, alginate, laminin, hyaluronans, silk, polyethylene glycol, isolated extracellular matrix hydrogels, or combinations thereof.

6. The composition of claim 1, wherein the plurality of cells are selected from the group consisting of: alpha cells, beta cells, delta cells, PP cells, epsilon cells, insulinoma cells, transgenic cells, knock-out cells, knock-in cells, or otherwise genetically modified cells, embryonic stem cells (ESCs), induced pluripotent stem cells (IPSCs), and combinations thereof.

7. The composition of claim 1, wherein the pancreatic islet cells are mammalian pancreatic islet cells selected from the group consisting of bovine, porcine, murine, rattus, equine, and human islet cells.

* * * * *